US011571539B2

(12) United States Patent
Barker et al.

(10) Patent No.: US 11,571,539 B2
(45) Date of Patent: Feb. 7, 2023

(54) FLUID MIXING STRUCTURE

(71) Applicant: Fisher & Paykel Healthcare Limited, Auckland (NZ)

(72) Inventors: Dean Antony Barker, Auckland (NZ); Russel William Burgess, Auckland (NZ); Peter Geoffrey Hawkins, Auckland (NZ); Maurice Wen-Bin Chai, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1320 days.

(21) Appl. No.: 14/805,298

(22) Filed: Jul. 21, 2015

(65) Prior Publication Data
US 2016/0082220 A1 Mar. 24, 2016

Related U.S. Application Data

(60) Provisional application No. 62/026,804, filed on Jul. 21, 2014.

(51) Int. Cl.
*A61M 16/12* (2006.01)
*A61M 16/10* (2006.01)
(Continued)

(52) U.S. Cl.
CPC ...... *A61M 16/125* (2014.02); *A61M 16/1005* (2014.02); *A61M 16/12* (2013.01);
(Continued)

(58) Field of Classification Search
CPC ................ A61M 16/125; A61M 16/12; A61M 16/1005; A61M 16/0066; A61M 2206/14;
(Continued)

(56) References Cited

U.S. PATENT DOCUMENTS 4,142,413 A * 3/1979 Bellinga ................. G01F 15/00
73/198
4,592,350 A * 6/1986 Maryyanek ............ A62B 23/02
128/206.17
(Continued)

FOREIGN PATENT DOCUMENTS

CA 2138686 8/1995
CA 2852215 4/2013
(Continued)

OTHER PUBLICATIONS

Jones, J. Lloyd, Flow Rotation Vanes Improve Piping Component Performance, The Pacific Energy Association Reporter, Summer Issue, 1992, vol. II, pp. 13-17.
(Continued)

*Primary Examiner* — Victoria Murphy
(74) *Attorney, Agent, or Firm* — Knobbe, Martens, Olson & Bear, LLP

(57) ABSTRACT

A respiratory therapy system can have a flow generator adapted to provide gases to a patient. A gas passageway can be located in-line with the flow generator. The gas passageway can have a first portion adapted to receive a first gas and a second portion adapted to receive a second gas. The gas passageway can have a static mixer downstream of the first and second portions.

23 Claims, 16 Drawing Sheets
(2 of 16 Drawing Sheet(s) Filed in Color)

(51) Int. Cl.
*A61M 16/16* (2006.01)
*B01F 23/10* (2022.01)
*B01F 25/421* (2022.01)
*B01F 35/213* (2022.01)
*B01F 35/22* (2022.01)
*B01F 35/221* (2022.01)
*A61M 16/00* (2006.01)

(52) U.S. Cl.
CPC ............ *A61M 16/16* (2013.01); *B01F 23/10* (2022.01); *B01F 25/4231* (2022.01); *B01F 35/213* (2022.01); *B01F 35/2202* (2022.01); *B01F 35/2211* (2022.01); *A61M 16/0066* (2013.01); *A61M 16/105* (2013.01); *A61M 16/109* (2014.02); *A61M 16/1095* (2014.02); *A61M 16/161* (2014.02); *A61M 2016/003* (2013.01); *A61M 2016/0027* (2013.01); *A61M 2016/102* (2013.01); *A61M 2016/103* (2013.01); *A61M 2016/1025* (2013.01); *A61M 2202/0208* (2013.01); *A61M 2205/3368* (2013.01); *A61M 2205/3375* (2013.01); *A61M 2206/11* (2013.01); *A61M 2206/14* (2013.01); *A61M 2230/04* (2013.01); *A61M 2230/10* (2013.01); *A61M 2230/201* (2013.01); *A61M 2230/202* (2013.01); *A61M 2230/205* (2013.01)

(58) Field of Classification Search
CPC . B01F 15/00207; F24F 13/28; B01D 46/0005
See application file for complete search history.

(56) References Cited

U.S. PATENT DOCUMENTS

| | | | |
|---|---|---|---|
| 5,093,058 A | 3/1992 | Harmon et al. | |
| 5,195,527 A * | 3/1993 | Hicks | A61M 16/106 128/205.27 |
| 5,495,872 A | 3/1996 | Gallagher et al. | |
| 5,529,093 A | 6/1996 | Gallagher et al. | |
| 5,792,229 A * | 8/1998 | Sassa | B01D 46/0001 55/497 |
| 5,992,413 A * | 11/1999 | Martin, Jr. | A61M 16/085 128/205.28 |
| 6,109,781 A | 8/2000 | Ogasawara et al. | |
| 8,651,800 B2 | 2/2014 | Li | |
| 2001/0033527 A1 | 10/2001 | Smith | |
| 2008/0035226 A1* | 2/2008 | Conrad | C02F 1/006 137/808 |
| 2011/0197882 A1* | 8/2011 | Truschel | A61M 16/202 128/204.18 |
| 2012/0104128 A1 | 5/2012 | Bara et al. | |
| 2013/0079667 A1 | 3/2013 | Berkcan et al. | |

FOREIGN PATENT DOCUMENTS

| | | | | |
|---|---|---|---|---|
| WO | WO-9203724 A1 * | 3/1992 | ........... G01N 29/024 |
| WO | WO-0045883 A1 * | 8/2000 | ............ A61M 16/00 |
| WO | WO-2013050907 A1 * | 4/2013 | ........ A61M 16/0891 |

OTHER PUBLICATIONS

Flaska, Kris and Kosla, Lee, Rotation Vanes Upstream of Pipe Elbows Improves Flow Meter Accuracy and Decreases Required Straight Pipe Meter Run Lengths, believed to have been available before Jul. 21, 2014.

X-Grid Static Mixer (Type GX) product, StaMixCo, http://www.stamixco-usa.com/x-grid, available before Jul. 21, 2014.

Koflo Static Mixer products, Burlington Pump Inc., http://www.process-controls.com/Burlington_Pump/koflo-sanitary-mixers.htm, available before Jul. 21, 2014.

* cited by examiner

FLUID MIXING STRUCTURE

CROSS-REFERENCE TO RELATED APPLICATIONS

The present application claims the priority benefit of U.S. Provisional Application No. 62/026,804, filed Jul. 21, 2014, the entirety of which is hereby incorporated by reference herein.

BACKGROUND

Technical Field

The present disclosure generally relates to respiratory therapy. More particularly, the present disclosure relates to structures for mixing gases used in respiratory therapy systems.

Description of the Related Art

A patient dealing with respiratory illness, for example chronic obstructive pulmonary disease (COPD), can have difficulty engaging in effective respiration. This difficulty may be the result of a variety of physiological faults, including a breakdown of lung tissue, dysfunctions of the small airways, excessive accumulation of sputum, infection, genetic disorders, or cardiac insufficiency. With some respiratory illnesses, it is useful to provide the patient with a therapy that can improve the ventilation of the patient. In some situations, the patient can be provided with a respiratory therapy system that includes a gas source, an interface that may be used to transmit gas to an airway of a patient, and a conduit extending between the gas source and the interface. Gas delivered to an airway of the patient from the gas source can help to promote adequate ventilation of the patient. The gas source may, for example, be a container of air and/or another gas suitable for inspiration, e.g. oxygen or nitric oxide, a mechanical blower capable of propelling a gas through the conduit to the interface, or some combination of both. The respiratory therapy system can include a gas humidifier that can humidify and heat gases passing through the respiratory therapy system to improve patient comfort and/or improve the prognosis of the patient's respiratory illness. The gas humidifier can include a water reservoir and a heating element for heating the water in the reservoir. As the water heats up, water vapor is formed, which can join the stream of gases passing through the gas humidifier.

If multiple gases, for example air and oxygen, are delivered to a patient using a respiratory therapy system, it is desirable to maintain control of the ratio of the gases delivered to the patient. If the ratio of oxygen to air is too high or, vice versa, if the ratio of air to oxygen is too high, the gas therapy may be less effective than desired. In some cases, a sensor adapted to measure the concentration of one or more of the gases passing through or along the respiratory therapy system can be used. The determined value for the concentration of gas can be used to control the supply of one or more of the gases to achieve the desired gas composition.

SUMMARY

It has been discovered that, in some cases, the accuracy of sensors used to measure the concentration of one or more gases passing through or along a gas passageway of a respiratory therapy system may be lower than desired, particularly if the gases fed to the sensor are not properly mixed. An ultrasonic transducer, for example, can be used to measure or estimate the composition of a gas mixture on a plane using a time-of-flight calculation. If, when using such a sensing arrangement, the gases composition in a given cross-section is such that the oxygen gas is substantially located in the plane of measurement and the air is substantially located outside of the plane of measurement, the true composition of the gases can be difficult to determine.

Certain features, aspects and advantages of at least one of the configurations disclosed herein include the realization that a respiratory therapy system may comprise a static mixer adapted to mix a pair of gases upstream of a gas composition sensing region. The static mixer may receive gas flows that are at least partially spaced apart and mix the gas flows. For example, the static mixer may receive gas flows that are at least in part vertically and/or horizontally spaced apart and mix the gas flows in a vertical and/or horizontal direction. The mixing may improve the accuracy of a gas composition sensor used in the gas composition sensing region.

Thus, in accordance with certain features, aspects and advantages of at least one of the embodiments disclosed herein, a flow mixer is disclosed. The flow mixer may be or may comprise a static mixer. The flow mixer may comprise a first baffle and a second baffle. The baffles may comprise or be substituted by other structures, such as plates, sheets, blocks, leaves, panes, slabs or panels. Each baffle may be positioned over a substantially horizontal plane in between a pair of substantially vertical planes. The first baffle may extend in a downstream direction at an angle offset from the horizontal plane. 'Downstream' in this sense may refer to the notion of the baffle extending in a direction that is the same or similar to the direction in which a gas flows through or along the mixer in use. The second baffle may be positioned downstream of the first baffle. 'Downstream' in this sense may refer to the notion that the second baffle may be positioned further along the flow path of gases passing through or along the flow mixer than the first baffle in use, which may be such that gases may pass over, along, or through the first baffle before reaching the second baffle in use. The second baffle may extend in a downstream direction at an angle offset from the horizontal plane. The first and second baffles may extend downstream or in a downstream direction at angles that are on opposing sides of the horizontal plane.

In some configurations, either the first or second baffles may extend downstream or in a downstream direction at angles offset from one or both of the vertical planes.

In some configurations, the first and second baffles may be linked by a bridge. The bridge may extend from about the middle of a downstream-pointing region of the first baffle to about the middle of an upstream-pointing region of the second baffle. The regions may be edges.

In some configurations, the first and second baffles may be linked by a first side rail extending across sides of the first and second baffles closest to one of the vertical planes. The first and second baffles may also be linked by a second side rail extending across the sides of the first and second baffles closest to the vertical plane away from the first side rail. The side rails may extend beyond the sides of the first baffle and join around an upstream-facing edge of the first baffle to define a wall and/or gases entry region. The gases entry region may comprise a flange. The flange may extend horizontally outside of one or both of the vertical planes. The flange may comprise a substantially trapezoidal shape, although other shapes can be envisioned, including rectangular or circular-shaped flanges.

In some configurations, a downstream side of the second baffle may taper inwardly.

Additionally, in accordance with certain features, aspects and advantages of at least one of the embodiments disclosed herein, a respiratory therapy system is disclosed. The respiratory therapy system may comprise a flow generator. The flow generator may be adapted to provide gases to a patient. The respiratory therapy system may comprise a gas passageway in-line with the flow generator. The gas passageway may comprise a first portion adapted to receive a first gas. The gas passageway may also comprise a second portion adapted to receive a second gas. The gas passageway may also comprise a flow mixer downstream of the first and second portions. The flow mixer may be or comprise a static mixer. The flow mixer may, for example, comprise or encompass one or more of the flow mixer configurations described above or elsewhere in this specification.

In some configurations, the gas passageway may be upstream of the flow generator.

In some configurations, the static mixer may substantially mix the first and second gases in a vertical direction.

In some configurations, a gas composition sensor may be located downstream of the static mixer. The gas composition sensor may be or may comprise an ultrasonic transducer. The ultrasonic transducer may emit and/or receive waves in a direction substantially perpendicular to the direction of gas mixing by the static mixer.

In some configurations, the flow generator may be pneumatically linked to a patient interface. In some configurations, the flow generator may be pneumatically linked to a gas humidifier.

In some configurations, a static flow mixer configured to mix multiple gases comprises an inlet configured to receive at least two gases, an outlet, a first baffle positioned between the inlet and the outlet, and a pinch. The pinch is defined between a downstream edge of the first baffle and a nearest downstream surface. A length of the pinch can be less than a height of the first baffle. In use, gases exiting the static mixer are substantially uniformly mixed.

In some such configurations, the first baffle extends at a first angle relative to horizontal upward and downstream relative to gases entering the inlet in use. The first angle can be in the range of 30° to 70°. The first angle can be in the range of 40° to 60°. The first angle can be 60°. In use, the first baffle can cause a gas flow through the static flow mixer to move upwards and then sharply turn at the downstream edge of the first baffle.

In some configurations, the static flow mixer further comprises a second baffle positioned between the first baffle and the outlet, wherein the pinch is defined by a line extending from the downstream edge of the first baffle to an upstream face of the second baffle and extending perpendicularly to the upstream face of the second baffle. In use, the first baffle can direct a flow of gases through the static mixer toward the second baffle. At least one of the first and second baffles can extend at an angle downstream. The second baffle can extend at a second angle relative to horizontal downward and downstream relative to the gases entering the inlet in use. The second angle can be in the range of 30° to 70°. The second angle can be in the range of 40° to 60°. The second angle can be 60°. In use, the second baffle can cause a gas flow through the static flow mixer to move downwards and then sharply turn at a downstream edge of the second baffle.

The length of the pinch can be less than half of the height of the first baffle. The length of the pinch can be in the range of one-third to one-fourth of the height of the first baffle. The length of the pinch can be about one-third of the height of the first baffle. In use, the pinch can accelerate a flow of gases passing through the static flow mixer. The length of the pinch can be uniform across a width of the pinch. In use, gases passing through the static flow mixer can swirl and expand after passing the first baffle and through the pinch. In some configurations, a second pinch is defined between a downstream edge of the second baffle and a bottom wall of the static flow mixer. In use, gases passing through the static flow mixer can swirl and expand after passing the second baffle and through the second pinch.

In some configurations, a bridge extends between and connects the first baffle and the second baffle. The bridge can split a flow of gases through the static mixer. The bridge can provide structural support to the static flow mixer.

In some configurations, at least a portion of at least one surface of the first baffle is roughened. In some configurations, at least a portion of at least one surface of at least one of the first and second baffles is roughened.

At least one of the at least two gases can be a therapeutic gas. The therapeutic gas can be oxygen. In use, the at least two gases can enter the inlet along different axes. In use, a flow of one of the at least two gases can be separated from a flow of another of the at least two gases as the gases enter the inlet. In use, the at least two gases can enter the inlet at opposite sides of the inlet.

In some configurations, the inlet defines a flange. The flange can be configured to aid insertion and retention of the static mixer in a housing.

A flow of gases entering the static flow mixer through the inlet can be laminar. A flow of gases exiting the static flow mixer through the outlet can be laminar. A flow of gases through the static flow mixer can have a Reynolds number less than 4000. A flow of gases through the static flow mixer can have a Reynolds number in the range of 35 to 2700. A flow of gases through the static flow mixer can have a Reynolds number in the range of 70 to 2700. A flow of gases through the static flow mixer can have a Reynolds number in the range of 70 to 2100. A flow of gases through the static flow mixer can have a Reynolds number in the range of 70 to 1000. A total volumetric flow rate through the static flow mixer can be in the range of 2 L min$^{-1}$ to 60 L min$^{-1}$. A total volumetric flow rate through the static flow mixer can be in the range of 2 L min$^{-1}$ to 25 L min$^{-1}$. A total volumetric flow rate through the static flow mixer can be in the range of 2 L min$^{-1}$ to 20 L min$^{-1}$. A total volumetric flow rate through the static flow mixer can be in the range of 25 L min$^{-1}$ to 60 L min$^{-1}$. A total volumetric flow rate through the static flow mixer can be in the range of 25 L min$^{-1}$ to 55 L min$^{-1}$. A total volumetric flow rate through the static flow mixer can be in the range of 30 L min$^{-1}$ to 55 L min$^{-1}$. A total volumetric flow rate through the static flow mixer can be in the range of 35 L min$^{-1}$ to 55 L min$^{-1}$. A total volumetric flow rate through the static flow mixer can be in the range of 40 L min$^{-1}$ to 50 L min$^{-1}$. A total volumetric flow rate through the static flow mixer can be in the range of 20 L min$^{-1}$ to 30 L min$^{-1}$. A volumetric flow rate of the therapeutic gas can be in the range of 5 L min$^{-1}$ to 60 L min$^{-1}$. A volumetric flow rate of the therapeutic gas can be in the range of 10 L min$^{-1}$ to 30 L min$^{-1}$. A volumetric flow rate of the therapeutic gas can be in the range of 15 L min$^{-1}$ to 25 L min$^{-1}$.

In some configurations, a respiratory therapy system comprises a flow generator, a first gas source configured to provide a first gas, a second gas source configured to provide a second gas, a gas passageway extending between the flow generator and the first and second gas sources, a static flow mixer, and at least one sensor. The static flow mixer is positioned in the gas passageway downstream of first and second gas sources and configured to mix gases supplied by the first and second gas sources at least by inducing swirling flow regions. The at least one sensor is positioned in the gas passageway downstream of the static mixer. The static mixer is configured to mix the gases supplied by the first and second gas sources to enable the sensor to provide more reliable readings. The static mixer can be configured to substantially uniformly mix the gases. The static flow mixer can be a static flow mixer as described herein.

The at least one sensor can be configured to measure a concentration of at least one gas flowing in the gas passageway downstream of the static mixer. The at least one sensor can comprise an ultrasonic transducer. The at least one sensor can comprise at least one temperature sensor. The at least one sensor can comprise at least one flow sensor. The at least one sensor can comprise a combination of temperature, flow, and/or ultrasonic sensors.

The static flow mixer can be configured to substantially uniformly mix the gases supplied by the first and second gas sources in a vertical direction. The static flow mixer can be configured to substantially uniformly mix the gases supplied by the first and second gas sources in a horizontal direction.

A local oxygen fraction in a gas flow in a region of the at least one sensor can be within ±10% $O_2$ of a bulk oxygen fraction of the gas in the gas passageway.

In some configurations, the respiratory therapy system further comprises a diffuser positioned between the static flow mixer and the sensor. The diffuser can be a honeycomb.

In some configurations, the respiratory therapy system further comprises a filter cover positioned in the gas passageway upstream of the static flow mixer. The filter cover can comprise prongs extending rearwardly from a front wall of the filter cover. The prongs can be configured to hold filter media in place and/or create a cavity between the filter cover and the filter media.

In some configurations, the respiratory therapy system further comprises a humidification apparatus. In some configurations, the respiratory therapy system further comprises a user interface. The user interface can be configured to display readings from the at least one sensor. In some configurations, the respiratory therapy system further comprises a controller. The controller can be configured to control a supply of at least one of the first and second gases from at least one of the first and second gas sources based on a measured concentration of the at least one of the first and second gases by the at least one sensor. The controller can be configured to control a concentration of gases delivered to a patient based on a measured concentration of at least one gas by the at least one sensor.

A size of the static flow mixer can be selected based on available space within the gas passageway.

The first gas source can comprise an inlet configured to receive ambient air. The second gas source comprises an inlet configured to receive a therapeutic gas. The therapeutic gas can be oxygen.

A flow of gases through the static flow mixer can be laminar. A flow of gases through the static flow mixer can have a Reynolds number less than 4000. A flow of gases through the static flow mixer can have a Reynolds number in the range of 35 to 2700. A flow of gases through the static flow mixer can have a Reynolds number in the range of 70 to 2700. A flow of gases through the static flow mixer can have a Reynolds number in the range of 70 to 2100. A flow of gases through the static flow mixer can have a Reynolds number in the range of 70 to 1000. A total volumetric flow rate through the static flow mixer can be in the range of 2 L $min^{-1}$ to 60 L $min^{-1}$. A total volumetric flow rate through the static flow mixer can be in the range of 2 L $min^{-1}$ to 25 L $min^{-1}$. A total volumetric flow rate through the static flow mixer can be in the range of 2 L $min^{-1}$ to 20 L $min^{-1}$. A total volumetric flow rate through the static flow mixer can be in the range of 25 L $min^{-1}$ to 60 L $min^{-1}$. A total volumetric flow rate through the static flow mixer can be in the range of 25 L $min^{-1}$ to 55 L $min^{-1}$. A total volumetric flow rate through the static flow mixer can be in the range of 30 L $min^{-1}$ to 55 L $min^{-1}$. A total volumetric flow rate through the static flow mixer can be in the range of 35 L $min^{-1}$ to 55 L $min^{-1}$. A total volumetric flow rate through the static flow mixer can be in the range of 40 L $min^{-1}$ to 50 L $min^{-1}$. A total volumetric flow rate through the static flow mixer can be in the range of 20 L $min^{-1}$ to 30 L $min^{-1}$. A volumetric flow rate of the therapeutic gas can be in the range of 5 L $min^{-1}$ to 60 L $min^{-1}$. A volumetric flow rate of the therapeutic gas can be in the range of 10 L $min^{-1}$ to 30 L $min^{-1}$. A volumetric flow rate of the therapeutic gas can be in the range of 15 L $min^{-1}$ to 25 L $min^{-1}$.

In some configurations, a static flow mixer configured to mix multiple gases comprises an inlet configured to receive at least two gases, an outlet, a first baffle positioned between the inlet and the outlet, and a second baffle positioned between the first baffle and the outlet. A pinch is defined by a line extending from the downstream edge of the first baffle to an upstream face of the second baffle and extending perpendicularly to the upstream face of the second baffle. A second pinch is defined between a downstream edge of the second baffle and a bottom wall of the static flow mixer.

The first baffle can extend at a first angle relative to horizontal upward and downstream relative to gases entering the inlet in use. The second baffle can extend at a second angle relative to horizontal downward and downstream relative to the gases entering the inlet in use. In use, the first baffle can cause a gas flow through the static flow mixer to move upwards and then sharply turn at the downstream edge of the first baffle and the second baffle can cause the gas flow through the static flow mixer to move downwards and then sharply turn at a downstream edge of the second baffle such that the gas flow is sharply turned no more than twice via the pinch and second pinch.

A length of the pinch can be less than a height of the first baffle. A length of the pinch can be less than half of a height of the first baffle. A length of the pinch can be in the range of one-third to one-fourth of a height of the first baffle. A length of the pinch can be about one-third of a height of the first baffle. A length of the pinch can be uniform across a width of the pinch.

In use, the pinch can accelerate a flow of gases passing through the static flow mixer. In use, gases passing through the static flow mixer can swirl and expand after passing the first baffle and through the pinch. In use, gases passing through the static flow mixer can swirl and expand after passing the second baffle and through the second pinch. The first and baffles can each extend past a central horizontal plane of the static flow mixer such that the first and second baffles provide a tortuous path for a flow of gases through the static flow mixer.

BRIEF DESCRIPTION OF THE DRAWINGS

The patent or application file contains at least one drawing executed in color. Copies of this patent or patent application publication with color drawing(s) will be provided by the Office upon request and patment of the necessary fee.

Specific embodiments and modifications thereof will become apparent to those skilled in the art from the detailed description herein having reference to the figures that follow, of which.

DETAILED DESCRIPTION

Figure 1:
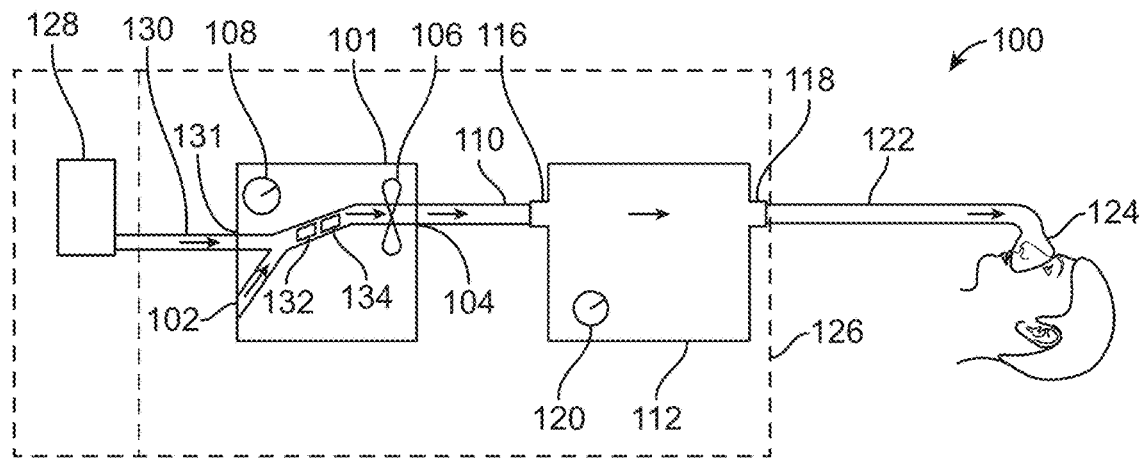
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101. The flow generator 101 may comprise a first gas inlet 102 and a gas outlet 104. The flow generator 101 may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the first gas inlet 102. The flow generator 101 may comprise a user interface 108 which may comprise one or more buttons, knobs, dials, switches, levers, touch screens, speakers, displays, and/or other input or output modules so that a user might use to input commands into the flow generator 101 to view data and/or control its operation and/or the operation of other aspects of the respiratory therapy system 100. The flow generator 101 may pass gas through the gas outlet 104 to a first conduit 110. The first conduit 110 may pass the gas to a humidifier 112 that may be used to entrain moisture in the gas in order to provide a humidified gas stream. The humidifier 112 may comprise a humidifier inlet 116 and a humidifier outlet 118. The humidifier 112 may comprise water or another moisturizing agent (hereinafter referred to as water). The humidifier 112 may also comprise a heating arrangement that may be used to heat the water in the humidifier 112 to encourage water vaporization and/or entrainment in the gas flow and/or increase the temperature of gases passing through the humidifier 112. The heating arrangement may, for example, comprise a resistive metallic heating plate. The humidifier 112 may comprise a user interface 120 which may comprise one or more buttons, knobs, dials, switches, levers, touch screens, speakers, displays and/or other input or output modules so that a user might use to input commands into the humidifier 112 to view data and/or control its operation and/or the operation of other aspects of the respiratory therapy system 100. Gas may then pass from the humidifier outlet 118 to a second conduit 122. The second conduit 122 may comprise a conduit heater. The conduit heater may be used to add heat to gases passing through the second conduit 122. The heat may reduce or eliminate the likelihood of the water entrained in the gas stream condensing along a wall of the second conduit 122. The conduit heater may comprise one or more resistive wires located in, on, around or near a wall of the second conduit 122. Gas passing through the second conduit 122 may then enter a patient interface 124 that may pneumatically link the respiratory therapy system 100 to an airway of a patient. The patient interface 124 may comprise a sealing or non-sealing interface, and may comprise a nasal mask, an oral mask, an oro-nasal mask, a full face mask, a nasal pillows mask, a nasal cannula, an endotracheal tube, a combination of the above or some other gas conveying system.

In the illustrated configuration, and as implied above, the respiratory therapy system 100 may operate as follows. Gas may be drawn into the flow generator 101 through the first gas inlet 102 due to the rotation of an impeller of the motor of the blower 106. The gas may then be propelled out of the gas outlet 104 and along the first conduit 110. The gas may enter the humidifier 112 through the humidifier inlet 116. Once in the humidifier 112, the gas may entrain moisture when passing over or near water in the humidifier 112. The water may be heated by the heating arrangement, which may aid in the humidification and/or heating of the gas passing through the humidifier 112. The gas may leave the humidifier 112 through a humidifier outlet 118 and enter a second conduit 122. Gas may be passed from the second conduit 122 to the patient interface 124, where the gas may be taken into the patient's airways to aid in the treatment of respiratory disorders.

The illustrated configuration should not be taken to be limiting; many other configurations for the respiratory therapy system 100 are possible. In some configurations, the flow generator 101 may, for example, comprise a source or container of compressed gas (e.g. air, oxygen, etc.). The container may comprise a valve that may be adjusted to control the flow of gas leaving the container. In some configurations, the flow generator 101 may use such a source of compressed gas and/or another gas source in lieu of the blower 106. In some configurations, the blower 106 may be used in conjunction with another gas source. For example, and as seen in FIG. 1, the respiratory therapy system 100 may comprise a second gas source 128. Gases from the second gas source 128 may enter the flow generator 101 through a conduit or gas passageway 130 leading to a second gas inlet 131. The second gas source 128 may comprise oxygen ($O_2$) or another gas suitable for respiration. The second gas source 128 may be directly connected to the flow generator 101, which may eliminate the need for the conduit or gas passageway 130, or the second gas source 128 may be connected to the respiratory therapy system 100 at other locations.

In some configurations, the blower 106 may comprise a motorized blower or may comprise a bellows arrangement or some other structure capable of generating a gas flow. In some configurations, the flow generator 101 may draw in atmospheric gases through the first gas inlet 102. In some configurations, the flow generator 101 may be adapted to both draw in atmospheric gases through the first gas inlet 102 and accept other gases (e.g. oxygen, nitric oxide, carbon dioxide, etc.) through the same first gas inlet 102. In some configurations, the flow generator 101 and the humidifier 112 may share a single housing 126. In some configurations, the flow generator 101, the humidifier 112, and the second gas source 128 may share a single housing 126.

In some configurations, the respiratory therapy system 100 may comprise a single user interface located on the first flow generator 101, the humidifier 112, the first conduit 110 or the second conduit 122, the patient interface 124, or another component of the respiratory therapy system 100. In some configurations, the operation of components of the respiratory therapy system 100 may be actuated wirelessly using a user interface located on a remote computing device, which may be a tablet, a mobile phone, a personal digital assistant, or another computing device. In some configurations, the operation of the flow generator 101, of the humidifier 112, or of other components or aspects of the respiratory therapy system 100 may be controlled by a controller. The controller may comprise a microprocessor. The controller may be located in or on the flow generator 101, the humidifier 112, or other components of the respiratory therapy system 100 or on a remote computing device. In some configurations, multiple controllers may be used.

In some configurations, the respiratory therapy system 100 may comprise one or more sensors for detecting various characteristics of gases in the respiratory therapy system 100, including pressure, flow rate, temperature, absolute humidity, relative humidity, enthalpy, gas composition, oxygen concentration, and/or carbon dioxide concentration, one or more sensors for detecting various characteristics of the patient or of the health of the patient, including heart rate, EEG signal, EKG/ECG signal, blood oxygen concentration, blood $CO_2$ concentration, and blood glucose, and/or one or more sensors for detecting various characteristics of gases or other objects outside the respiratory therapy system 100, including ambient temperature and/or ambient humidity. One or more of the sensors of the respiratory therapy system 100, which can be located, for example, in or on the flow generator 101, in or on the humidifier 112, and/or in or on the patient interface 124, may be used to aid in the control of components of the respiratory therapy system 100 through the use of a closed or open loop control system. For example, the flow generator 101 may comprise a gas composition sensor 134. The gas composition sensor 134 may comprise an ultrasonic transducer.

In some configurations, there may be no user interface or a minimal user interface for components of the respiratory therapy system 100. In some such configurations, the respiratory therapy system 100 may utilize a sensor to determine if the patient is attempting to use the respiratory therapy system 100 and automatically operate (e.g., the flow generator 101 may generate a gas flow, the humidifier 112 may humidify gases, etc.) according to one or more predetermined parameters if data obtained from the sensor indicates that the patient is attempting to use the respiratory therapy system 100.

If two gas sources are used as shown in FIG. 1 (e.g. ambient gases entering the flow generator 101 from the first gas inlet 102 and gases from the second gas source 128 entering the flow generator 101 from the second gas inlet 131), a gas mixer or flow mixer 132 may be located downstream of the gas sources. The gas mixer 132 may be used to mix the gases or move the gases relative to one another. The gas mixing may help to promote breath-by-breath consistency in the gas composition delivered to the patient, which may improve the therapeutic benefit of the respiratory therapy, and/or the gas mixing may help to improve the accuracy of the gas composition sensor 134, which may be downstream of the gas mixer 132. The gas mixer 132 may comprise a static mixer. 'Static mixer', as shown and described in the accompanying disclosure, may be understood to refer to structures having no moving parts that promote the mixing of gases or other fluids by utilizing the energy of the gases rather than utilizing energy from another source (e.g., an electrical power supply). Further details on this configuration are given elsewhere in the disclosure.

Further attention is given to the gas mixer 132 or other gas mixers, and more particularly to static mixers. FIGS. 2A-2G demonstrate a static mixer 200. The static mixer 200 may comprise an inlet frame 202. The inlet frame 202 may define an aperture that receives the gas flow. The inlet frame 202 may have an outer flange 204. The outer flange 204 can be adapted to assist in retaining the static mixer 200 in a gas passageway of a respiratory therapy system as later described in this disclosure. The inlet frame 202 may comprise a projection 206. The projection 206 may extend from a part of a wall of the inlet frame 202 in a direction downstream of and generally parallel to the direction of gas flow into the static mixer 200 in use. The projection 206 may be linked to a first sloping section or baffle 208. As shown, the first sloping section 208 is disposed at an angle such that the first sloping section 208 extends downward and forward relative to an axis extending through the inlet frame 202 or relative to the direction of gas flow entering the static mixer 200 through the aperture in the inlet frame 202 in use. The first sloping section 208, in use, may drive the gases entering the static mixer 200 vertically downwards as the flow progresses forward. The static mixer 200 can further comprise a second sloping section or baffle 212 positioned downstream of the first sloping section 208. As shown, the second sloping section 212 is disposed at an angle such that the second sloping section 212 extends generally upward and forward relative to the axis extending through the inlet frame 202. Gases driven down by the first sloping section 208 may then be substantially guided vertically upwards as the flow progresses forward by the second sloping section 212 and exit the static mixer 200 through an outlet section 214. In some embodiments, for example as described herein, a static mixer may include fewer or more than two baffles, and/or the baffles may have other configurations. For example, in some embodiments, a first baffle may extend upward and forward and a second baffle may extend downward and forward relative to the flow of gases entering the static mixer 200 in use. In such configurations, such as those shown in FIGS. 3C, 3G, 4 and 5A-5D, for example but without limitation, the flow may be driven vertically upwards as the flow progresses forward and then vertically downwards. Other configurations are also possible. Furthermore, the static mixer 200, or other static mixers according to the present disclosure, could be rotated or positioned in different orientations in use.

The static mixer 200 may also comprise side walls 210. The side walls 210 may aid in guiding the gas flow and/or retaining the static mixer 200 in the gas passageway of a respiratory therapy system. In the illustrated embodiment, the first sloping section 208 and second sloping section 212 extend between and are attached to the sidewalls 210. Although the accompanying figures disclose that the illustrated static mixer 200 comprises two side walls 210, it should be understood that in some configurations the static mixer 200 may only comprise a single side wall 210 or more than two side walls 210. In some configurations, the first and second sloping sections 208, 212 may be physically linked and no side walls 210 need be used.

It should be understood that the static mixer 200 may have other configurations. For example, and as shown in FIG. 2F, the static mixer 200 may lack a projection 206. In some configurations, some or all of the sections of the static mixer 200, including but not limited to one or both of the sloping sections 208, 212, may instead be integrally formed with a gas passageway of a respiratory therapy system.

Figure 2A:
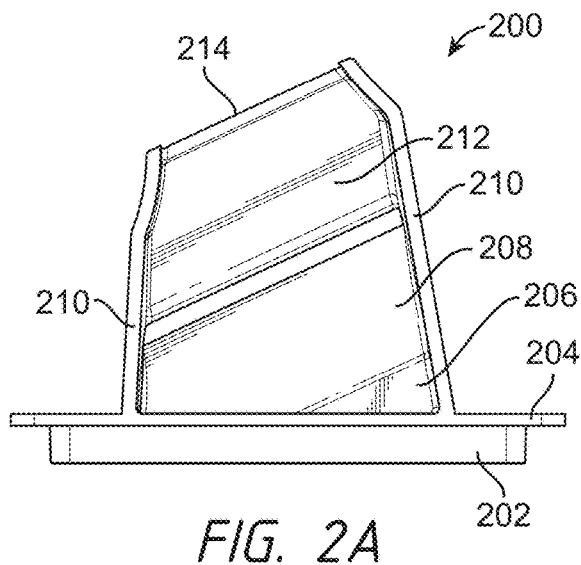
FIG. 2A shows a top plan view of a flow mixer.
Figure 2B:
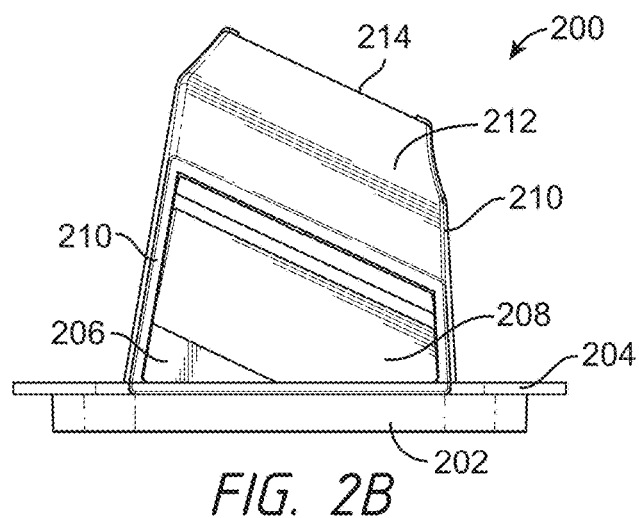
FIG. 2B shows a bottom plan view of the flow mixer of FIG. 2A.
Figure 2C:
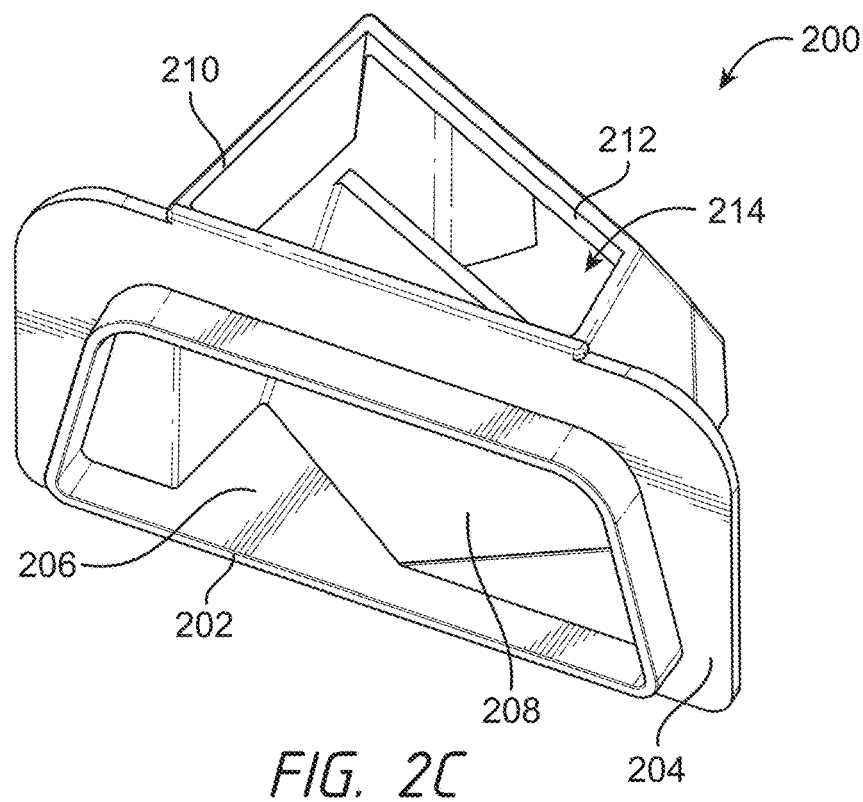
FIG. 2C shows a bottom perspective view of the flow mixer of FIG. 2A.
Figure 2D:
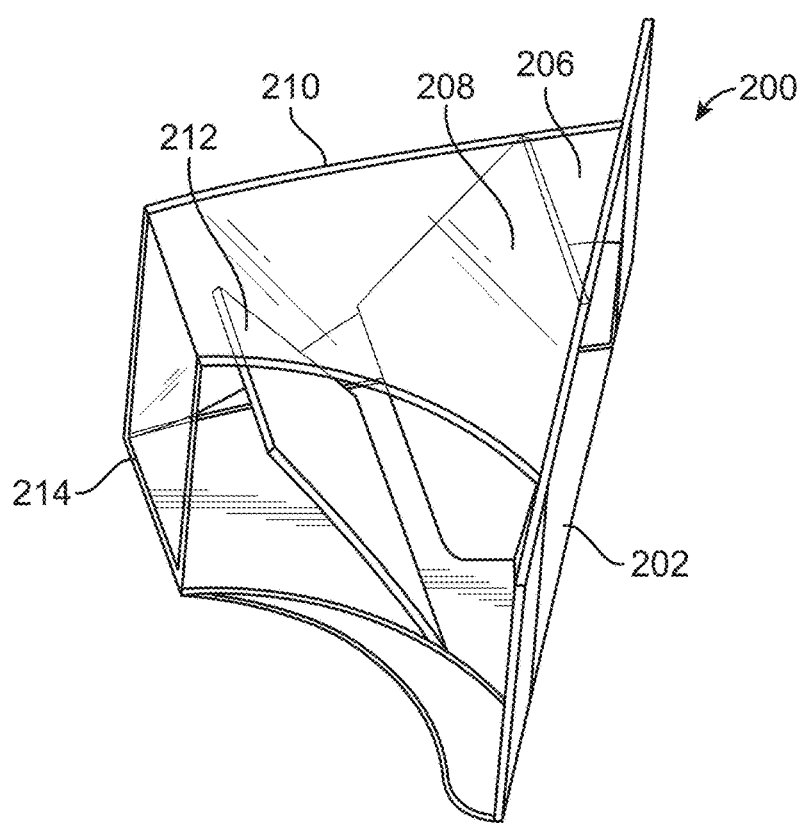
FIG. 2D shows a model of a perspective view of the flow mixer of FIG. 2A.
Figure 2E:
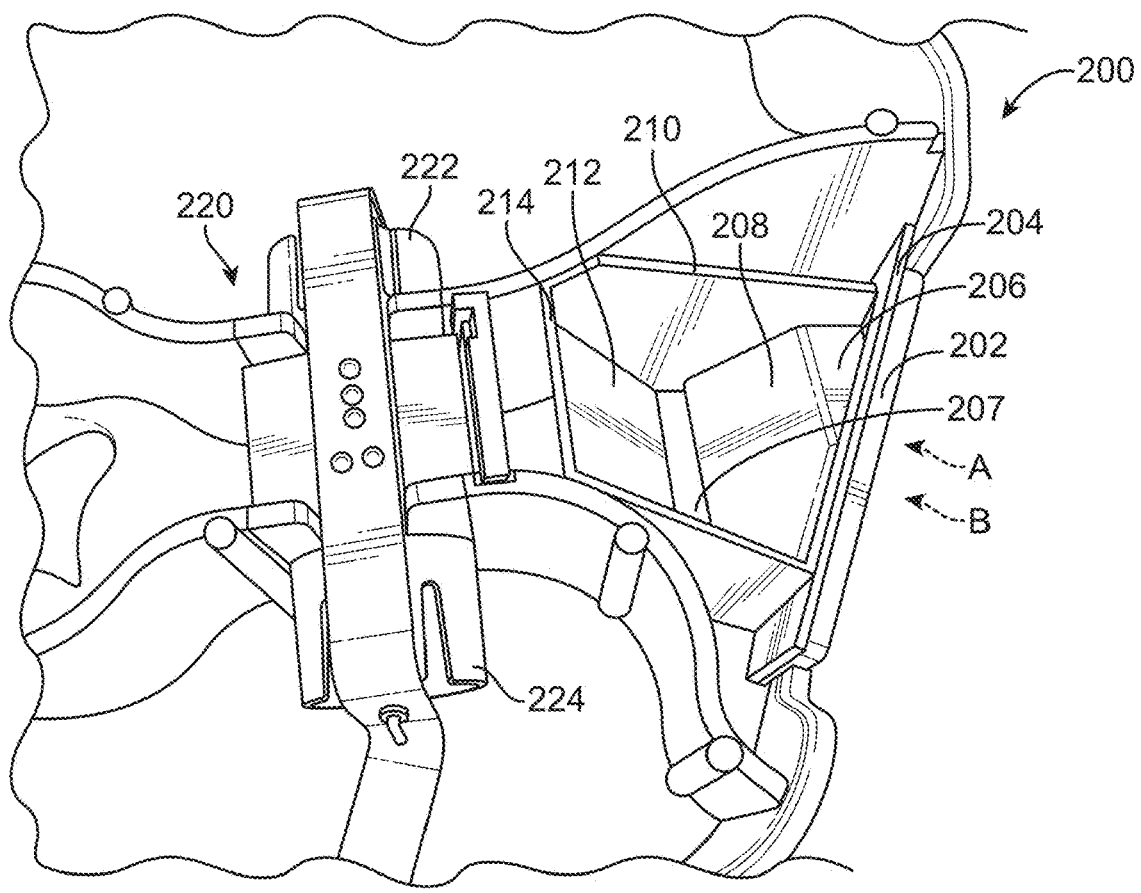
FIG. 2E shows a section of a respiratory therapy system comprising the flow mixer of FIG. 2A.
Figure 2F:
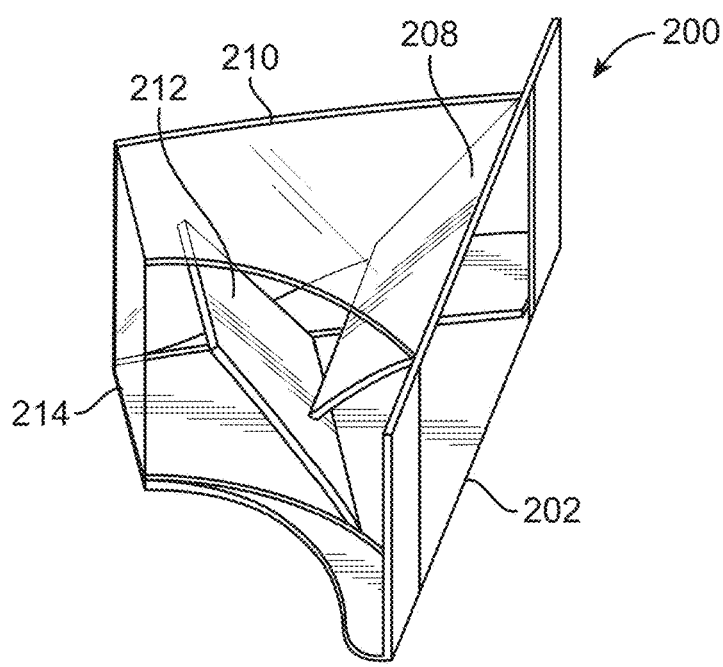
FIG. 2F shows a model of a perspective view of a flow mixer similar to the flow mixer shown in FIG. 2D.

FIG. 2E demonstrates how the static mixer 200 may be positioned in a respiratory therapy system. In particular, FIG. 2E shows that the static mixer 200 may be placed within a gas passageway of a respiratory therapy system. In the illustrated configuration, and as implied in FIG. 1, the static mixer 200 may be located upstream of a blower. The outer flange 204 of the static mixer 200 may help to retain the static mixer 200 in a desired position, as shown. Dashed arrow A shows gas from a first gas source (e.g. ambient air) passing into the static mixer 200 and dashed arrow B shows gas from a second gas source (e.g. oxygen ($O_2$) gas) passing into the static mixer 200. The gases may enter the static mixer 200 in directions at least partially substantially vertically parallel to one another (e.g., the 'A' gas may enter the static mixer 200 at a position substantially vertically higher than the 'B' gas, or vice versa). In some embodiments, the gases may enter the static mixer 200 in directions at least partially horizontally parallel to one another. In some embodiments, the gases may enter the static mixer 200 in directions vertically and/or horizontally offset from one another. In some configurations, the gases may enter the static mixer 200 with differing axes of flow. In some configurations, the gases may enter the static mixer 200 with parallel axes of flow. In some configurations, the gases may enter the static mixer 200 with angularly offset axes of flow.

An ultrasonic transducer 220 may be positioned downstream of the static mixer 200. The ultrasonic transducer 220 may comprise a first region 222 and a second region 224. Each of the first and second regions 222, 224 may comprise a wave transmitter and a wave receiver. The first region 222 may generate an ultrasonic wave that may travel transversely to be received at the second region 224, or vice versa. The time taken for the wave emitted by the first region 222 to reach the second region 224 may be calculated and a signal may be transmitted to a controller controlling the delivery of gases from the first and/or second gas sources. If the 'A' gas and the 'B' gas are different and both are known, the time-of-flight of the wave, in this case, may change depending on the proportions of the 'A' gas and the 'B' gas in the path of the transverse wave—thus, the composition of the gases may be determined. The controller may directly or indirectly compare the signal to one or more input conditions (e.g., a desired gas composition or ratio to be delivered to a patient) and alter the supply of gases from the first and/or second gas sources as desired (e.g., through the use of a closed loop or proportional-integral-derivative control system). It should be understood that other gas composition sensors may be substituted for the ultrasonic transducer 220. In addition, the ultrasonic transducer may operate in different ways—for example, the ultrasonic transducer may only comprise a wave transmitter and a wave receiver in the first region 222, and the second region 224 may only be configured to reflect the transmitted wave back to the first region.

Figure 2G:
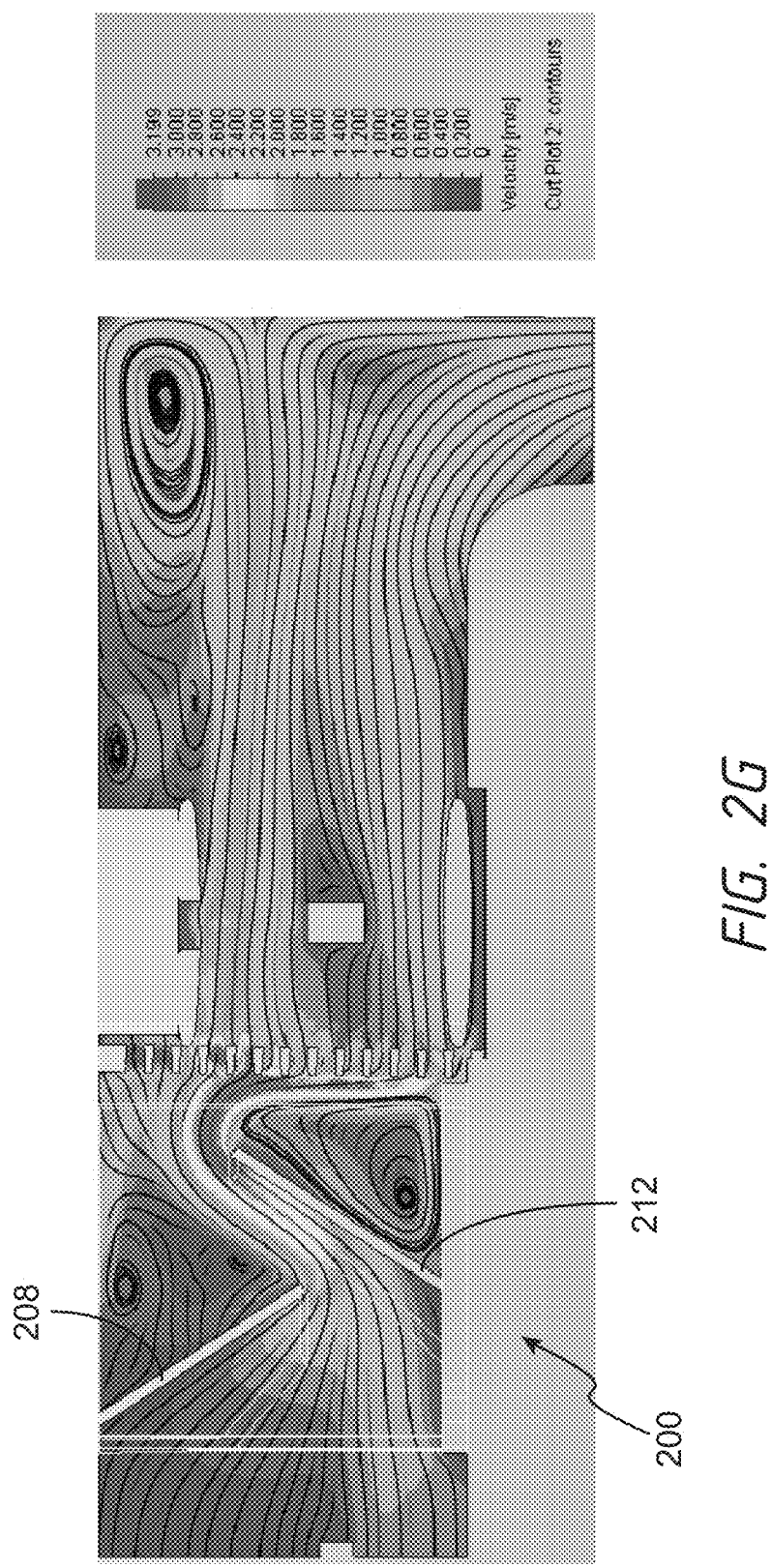
FIG. 2G shows a computer-generated model of gas flow passing along a model of the flow mixer of FIG. 2A.
Figure 2H:
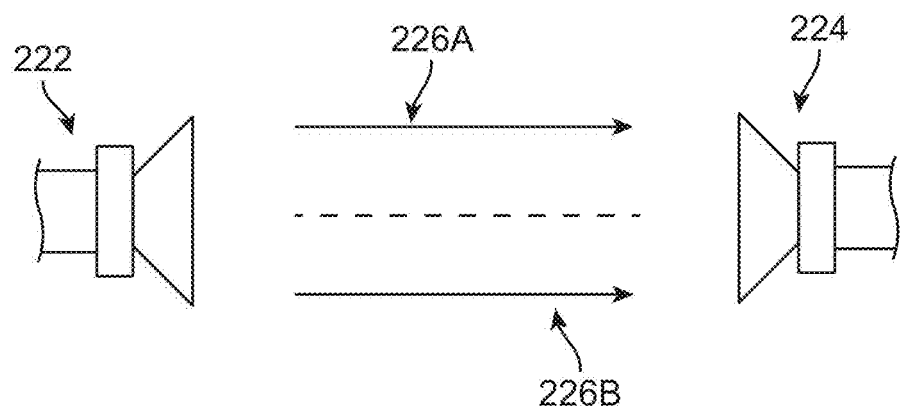
FIG. 2H shows a schematic of an ultrasonic transducer being used to measure the gas composition of a gas mixture where the gases are separated vertically.
Figure 2I:
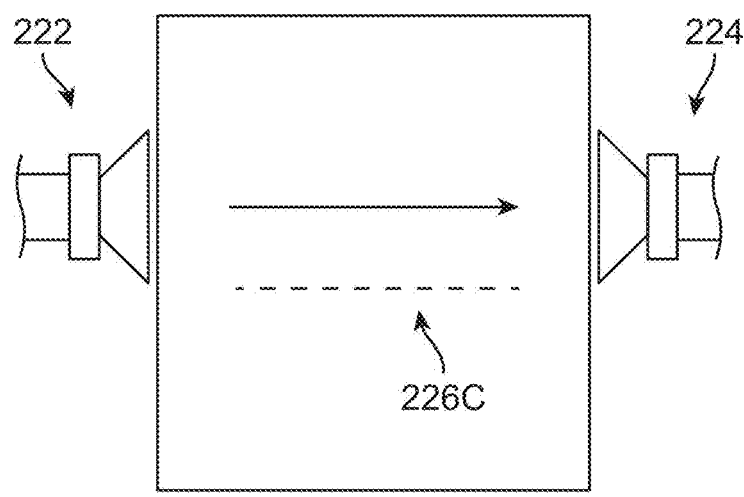
FIG. 2I shows a schematic of an ultrasonic transducer being used to measure the gas composition of a gas mixture where one gas is outside of the acoustic path.

The static mixers 200 as shown in FIGS. 2A-2G may be particularly advantageous if used with the ultrasonic transducer 220 with gases 'A' and 'B' as shown in FIG. 2E. In the given configuration, the ultrasonic transducer 220 may only substantially emit and receive ultrasonic waves across a relatively narrow horizontal plane. Considering that gases 'A' and 'B' are vertically spaced, if the static mixer 200 is not present, the signal obtained by the ultrasonic transducer 220 may not represent the composition of the gases passing through the ultrasonic transducer 220 as accurately as desired. For example, as shown in the schematic of FIG. 2H, if the flow of gas A is vertically spaced from and higher than the flow of gas B when the gas flow passes through the ultrasonic transducer 220, the different speeds of sound of the gases will result in two pulses, pulse 226A passing through gas A and pulse 226B passing through gas B, arriving at the receiver 224 at different times, which will produce an inaccurate reading. In some cases, for example as shown in the schematic of FIG. 2I, poor gas mixing can result in one gas being outside of the acoustic path of the ultrasonic transducer 220, as indicated by dashed line 226C. In that case, the ultrasonic transducer 220 would measure the speed of sound only through the gas within the acoustic path.

However, if the illustrated static mixer 200, or another static mixer according to the present disclosure, is used, gases 'A' and 'B' may vertically collate as they move along the first and second sloping sections 208, 212, which may improve the accuracy of the gas composition detection. The static mixer 200, or another static mixer according to the present disclosure, can also be advantageous when used with gases that are horizontally spaced instead of or in addition to being vertically spaced, or with gases that are not substantially spaced and/or are at least partially premixed before entering the static mixer, to further mix the gases and improve sensor readings. FIG. 2G shows a computational fluid dynamics model depicting a side cross-sectional view of a gas passageway of a respiratory therapy system comprising a static mixer 200, where air and oxygen gas move through the gas passageway along the black arrows as illustrated. As noted, the flow lines change as the gases move along the first and second sloping sections 208, 212, indicating improved gas mixing. The flow lines show the direction of flow at each point, and thereby show where the swirl occurs. The color indicates the velocity of the gas flow as shown in the key in FIG. 2G. As shown, the velocity increases as the gases pass through the pinches, described in greater detail herein. Additionally, flow vortices and/or eddies may be created over and/or under the second sloping section 212, which can generate increases in vorticity that may promote gas mixing.

Figure 3A:
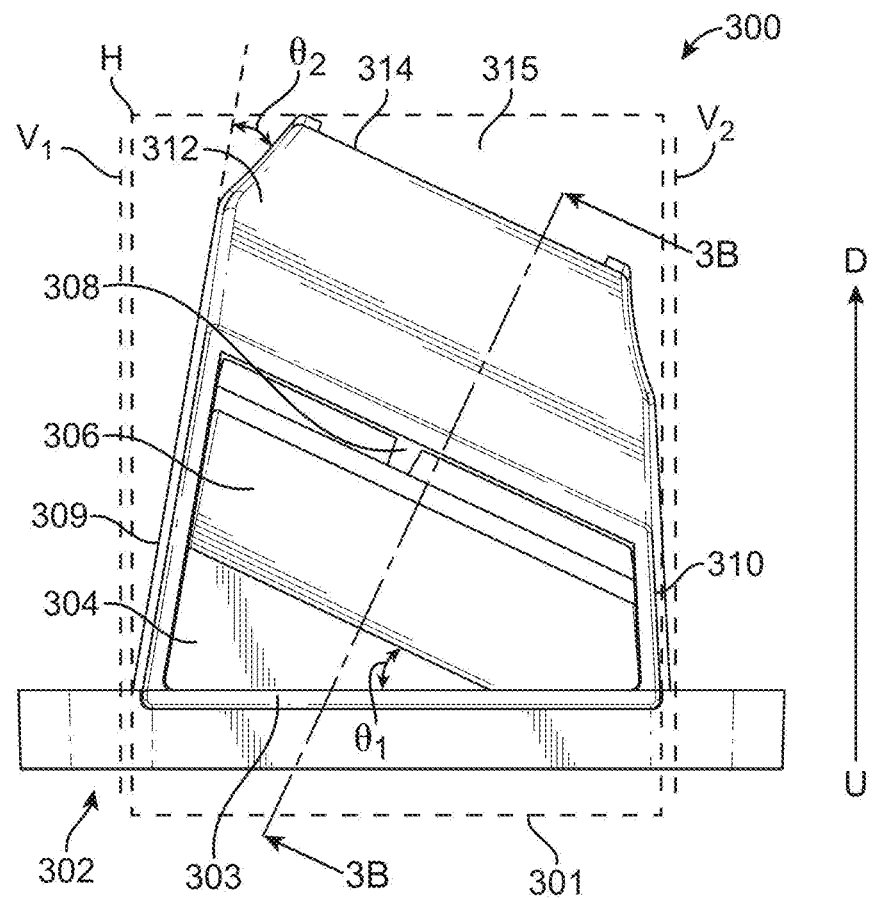
FIG. 3A shows a top plan view of an alternative flow mixer similar to that shown in FIG. 2A.

Other static mixers may be used instead of or in combination with the static mixers described relative to FIGS. 2A-2G. FIGS. 3A-3H illustrate another flow mixer 300 having a configuration similar to that disclosed for the static mixers described above. Similarly, the flow mixer 300 may be or comprise a static mixer. For the sake of convenience, and as illustrated in FIG. 3A, the structure of the flow mixer 300 may be described with reference to a Euclidean space constructed using an imaginary horizontal plane H and two imaginary vertical planes $V_1$, $V_2$ (which in FIG. 3A can be imagined to project outwardly from the page). Additionally the flow mixer 300 may be described with respect to an upstream direction U and a downstream direction D as noted in FIG. 3A, where downstream in this case can refer to the direction in which gases generally flow through the flow mixer 300 in use. In FIGS. 3A-3F, numerals corresponding to lengths, widths, heights or other physical dimensions of components of the illustrated flow mixer 300 are in millimeters, although it should be understood that the dimensions shown may vary and are not necessarily limited to the values shown. Numerals corresponding to angles between components of the illustrated flow mixer 300 are shown in degrees, although it should be understood that the angles shown may vary and are not necessarily limited to the values shown.

As shown, the flow mixer 300 may comprise a first baffle 306 and a second baffle 312 The baffles 306, 312 may be placed in series, or such that one baffle may be placed further along or downstream of the flow path of gases passing through the flow mixer 300 in use than the other baffle. The first baffle 306 may extend in the downstream direction at an angle offset from the direction of flow D. The first baffle 306 may be angled to any desired angle. For example, in the configuration of FIG. 3A, the first baffle 306 may project downstream at an angle that is 35° to 85° offset from the direction of flow D through the gases entry region 301, or 40° to 80°, or 45° to 75°, or 50° to 70°, or 55° to 65°, or 60°. This angle corresponds to $\theta_A$ in the embodiment shown in FIG. 4. Similarly, the second baffle 312 may extend in the downstream direction at an angle offset from the direction of flow D. For example, the second baffle 312 may project downstream at an angle that is 35° to 85° offset from the direction of flow, or 40° to 80°, or 45° to 75°, or 50° to 70°, or 55° to 65°, or 60°. This angle corresponds to angle $\theta_B$ in the embodiment shown in FIG. 4. In some configurations, the first baffle 306 and the second baffle 312 may extend downstream at angles that originate from opposing walls or surfaces that define the flow passage. For example, and as demonstrated in FIGS. 3A-3F, the first baffle 306 may extend downstream and upwardly, while the second baffle 312 may extend downstream and downwardly. Alternatively, the first baffle 306 may extend downstream and downwardly, and the second baffle 312 may extend downstream and upwardly. Additionally, and as demonstrated in FIGS. 3A-3F, the first and second baffles 306, 312 may be offset in the flow direction D with respect to their starting position. In the configuration shown most clearly in FIG. 3B, an upstream edge of the second baffle 312 and a downstream edge of the first baffle 306 may be approximately 6.5 mm apart with the upstream edge of the second baffle 312 positioned downstream of the downstream edge of the first baffle 306. Alternatively, the magnitude of the offset between the first and second baffles 306, 312 may be different, or there may be no offset between the baffles 306, 312.

As demonstrated most clearly in FIG. 3A, the first baffle 306 may extend in a downstream direction at an angle offset from one of the vertical planes $V_1$, $V_2$. In other words, the first baffle 306 may be angled with respect to the vertical planes $V_1$, $V_2$, for example due to a projection 304 extending from a gases entry region 301 that forces the baffle 306 to extend downstream at an angle $\theta_1$. Additionally, the second baffle 312 may extend in a downstream direction at an angle. The baffles 306, 312 may have the same or different angles. Alternatively, in some configurations one or both of the baffles 306, 312 can have no such offset.

The downstream side or edge of the second baffle 312 may taper inwardly to an edge region 314 towards a gases exit region or outlet 315. For example, and as demonstrated most clearly in FIG. 3A, the second baffle 312 may angularly extend inwardly at an angle $\theta_2$ from an upstream portion or region of the second baffle 312 on the side of the second baffle 312 closest to one of the vertical planes $V_1$, $V_2$ (here, $V_1$). Additionally, the other side of the second baffle (here, the side closest to the other vertical plane $V_2$) may taper inwardly. The taper may begin at approximately the same point along the other side of the second baffle 312 as along the side closest to the first side closest to the vertical plane $V_1$, but may alternatively begin at a different point. The taper angle may likewise be the same or different as the angle $\theta_2$. Alternatively, in some configurations one or both of the downstream sides or edges of the second baffle 312 may have no such taper.

In the embodiment shown in FIG. 3A, the direction of flow of the gas exiting the mixer is offset from the direction of flow of the gas entering the mixer. The direction of flow is initially turned by $\theta_1$ and then turned by $\theta_2$.

A bridge 308 may link the first and second baffles 306, 312. The bridge 308 may comprise a segment of material that physically connects the first and second baffles 306, 312. The bridge 308 may extend from about the middle of a downstream-pointing region of the first baffle 306 to about the middle of an upstream-pointing region of the second baffle 312. For example, the bridge 308 may extend from the downstream-pointing edge of the first baffle 306 to the upstream-pointing edge of the second baffle 312. The bridge 308 may help to provide improved gas mixing by bisecting incoming flow, which may increase gas vorticity. The bridge 308 can also provide support to the baffles 306, 312 to prevent the baffles bending in use. Other configurations for the bridge 308 may be envisioned. For example, the bridge 308 could be ribbed or have rough projections that could improve gas mixing. Multiple bridges could extend between the first and second baffles 306, 312. In addition, in some configurations the bridge 308 or multiple bridges may extend between the baffles 306, 312 at angles that deviate from the directions in which the first and/or second baffles 306, 312 extend. In some embodiments, a static mixer according to the present disclosure does not include a bridge, for example, as shown in the embodiment of FIGS. 2A-2H.

The first and second baffles 306, 312 may be linked by a first side rail or side wall 309. The first side rail 309 may extend across the sides of the first and second baffles closest to the vertical plane $V_1$. The first and second baffles 306, 312 may be linked by a second side rail or side wall 310. The second side rail 310 may extend across the sides of the first and second baffles closest to the vertical plane $V_2$. If both of the side rails 309, 310 are present, and as demonstrated most clearly in FIG. 3C, the side rails 309, 310 may extend beyond the sides of the first baffle 306 and join around the upstream-facing edge of the first baffle 306 to form a wall 303. The wall 303 may comprise an aperture that defines or forms a gases entry region 301. The gases entry region 301 may comprise a flange 302. The flange 302 may extend horizontally outside of one or both of the vertical planes $V_1$, $V_2$. The flange 302 may comprise a top wall 302A, a bottom wall 302C, and side walls 302B, 302D, which may collectively give the flange 302 a roughly trapezoidal shape, although other shapes such as rectangular or circular shapes can be envisioned. Additionally, and as demonstrated most clearly in FIGS. 3A and 3D, one or both of the side rails 309, 310 may taper inwardly in a downstream region concurrently or non-concurrently with the second baffle 312. In some configurations, one or both of the side rails 309, 310 may not be present. In some such configurations, the first and second baffles 306, 312 may be linked or supported via some other arrangement.

Therefore, in the illustrated embodiment, the wall 303 can be considered a front wall of the flow mixer 300, and side walls 309, 310 are attached to side edges of and extend rearwardly from the front wall 303. The first baffle 306 is attached to and extends between the side walls 309, 310. The second baffle 312 is attached to and extends between rear edges of the side walls 309, 310 and can define a rear wall of the flow mixer 300. The outlet 315 can be defined by the bottom edge 314 of second baffle 312 and bottom portions of the rear edges of the side walls 309, 310 as shown in FIG. 3H. In the illustrated embodiment, the first baffle 306, second baffle 312, and outlet 315 are positioned at an angle relative to a plane perpendicular to the flow of gases entering the flow mixer 300. The projection 304 extends from the bottom wall 302C of the flange 302 to a bottom edge of the first baffle 306 and directs gases entering the flow mixer 300 to the first baffle 306 in use (i.e., the projection 304 prevents gases from passing downward and below a bottom edge of the first baffle 306). The baffles 306, 312 may be positioned at an angle to fit within the flow path of the particular system and/or based on the position of the sensor 134 relative to the flow mixer 300. However, in other embodiments, the first baffle 306, second baffle 312, and/or outlet 315 can be perpendicular to the flow of gases entering the flow mixer 300 and still promote mixing of the gases. The first baffle 306 and second baffle 312 can act as a labyrinth, which can promote mixing. The first baffle 306 and second baffle 312 can provide a tortuous path for gases flowing through the flow mixer 300. In some embodiments, the flow mixer 300 can include more than two baffles.

Figure 3B:
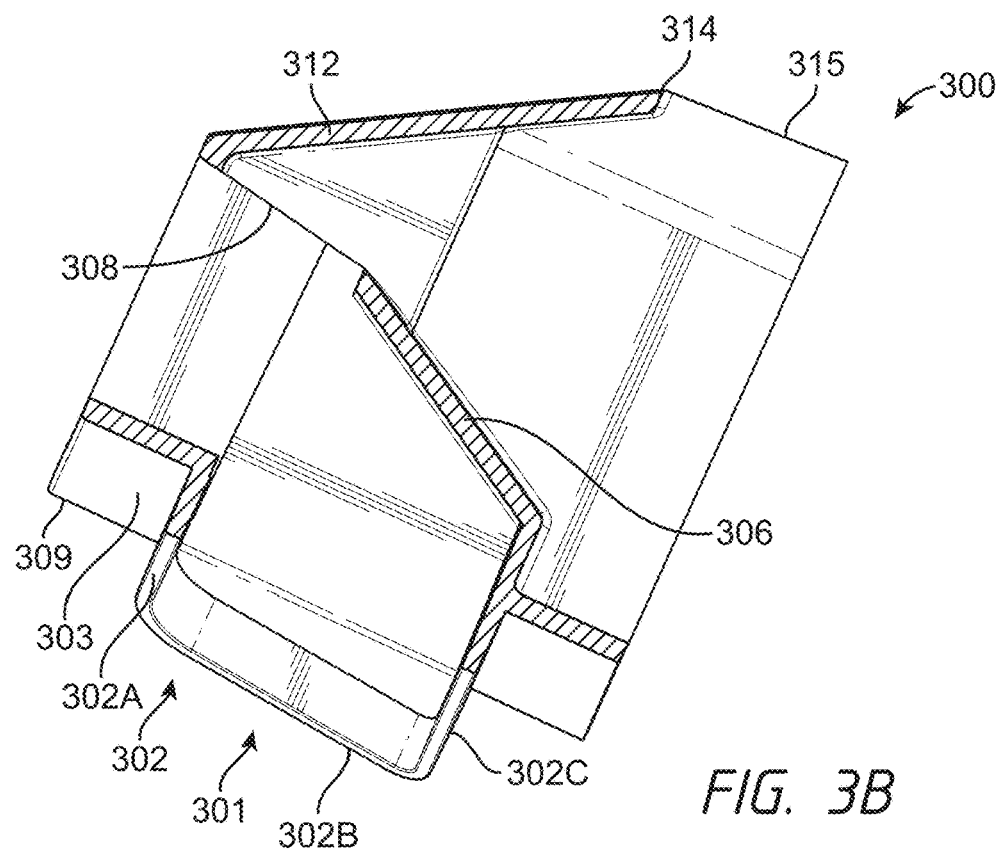
FIG. 3B shows a cross-sectional view of the flow mixer of FIG. 3A along section 3B-3B.
Figure 3C:
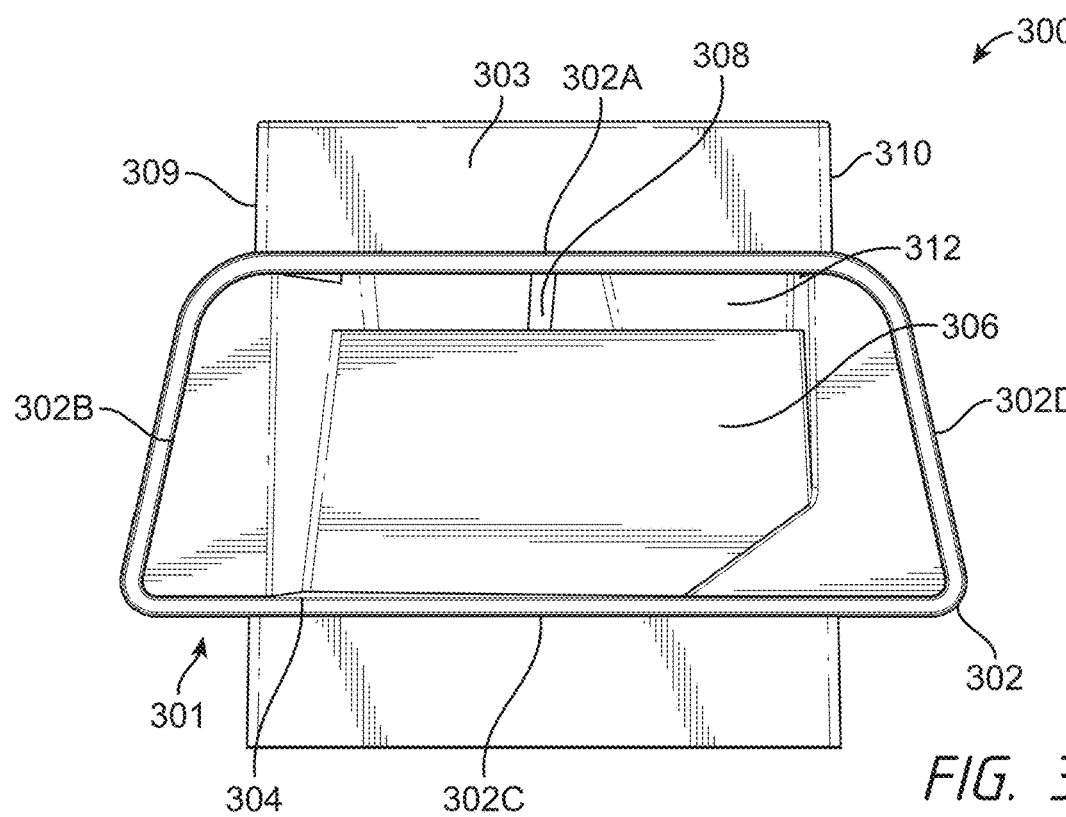
FIG. 3C shows a front view of the flow mixer of FIG. 3A.
Figure 3D:
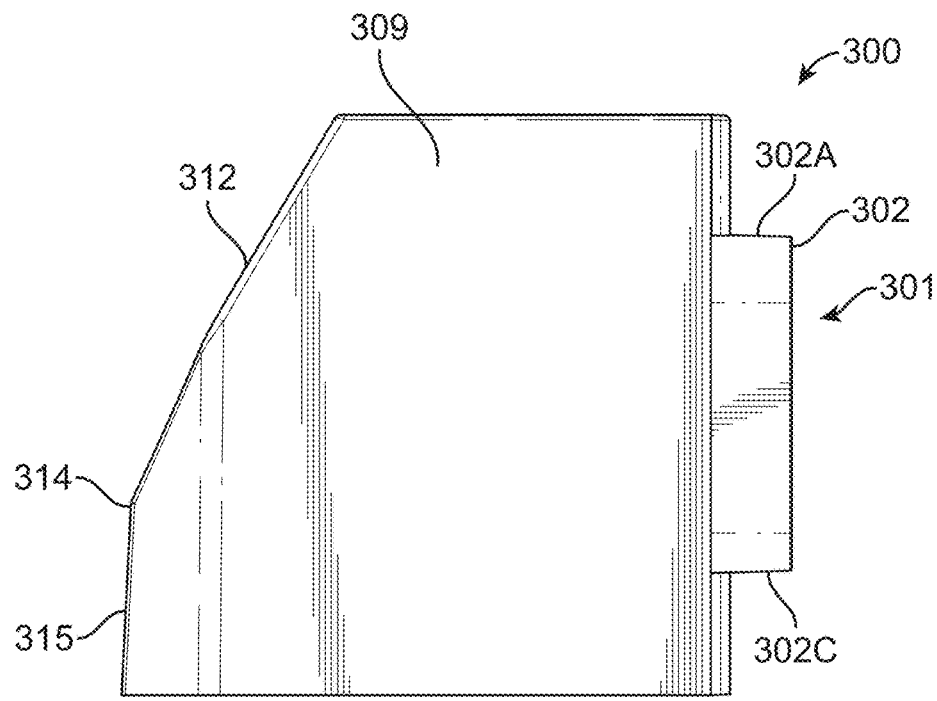
FIG. 3D shows a left side view of the flow mixer of FIG. 3A.
Figure 3E:
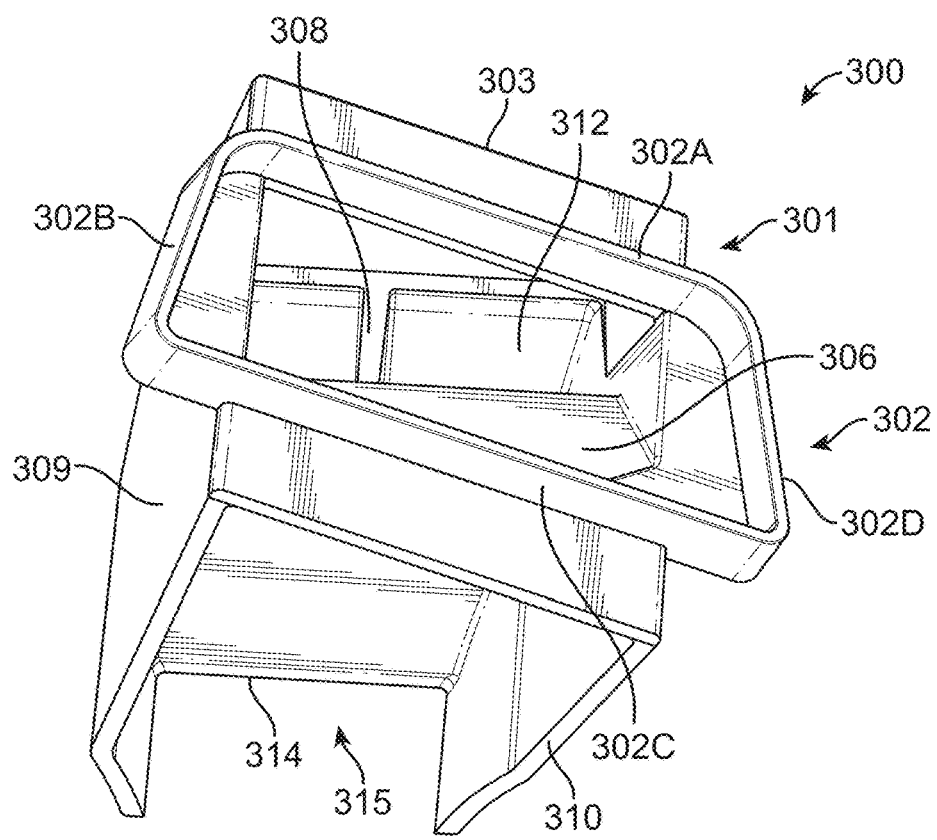
FIG. 3E shows a bottom-front view of a model of the flow mixer of FIG. 3A.
Figure 3F:
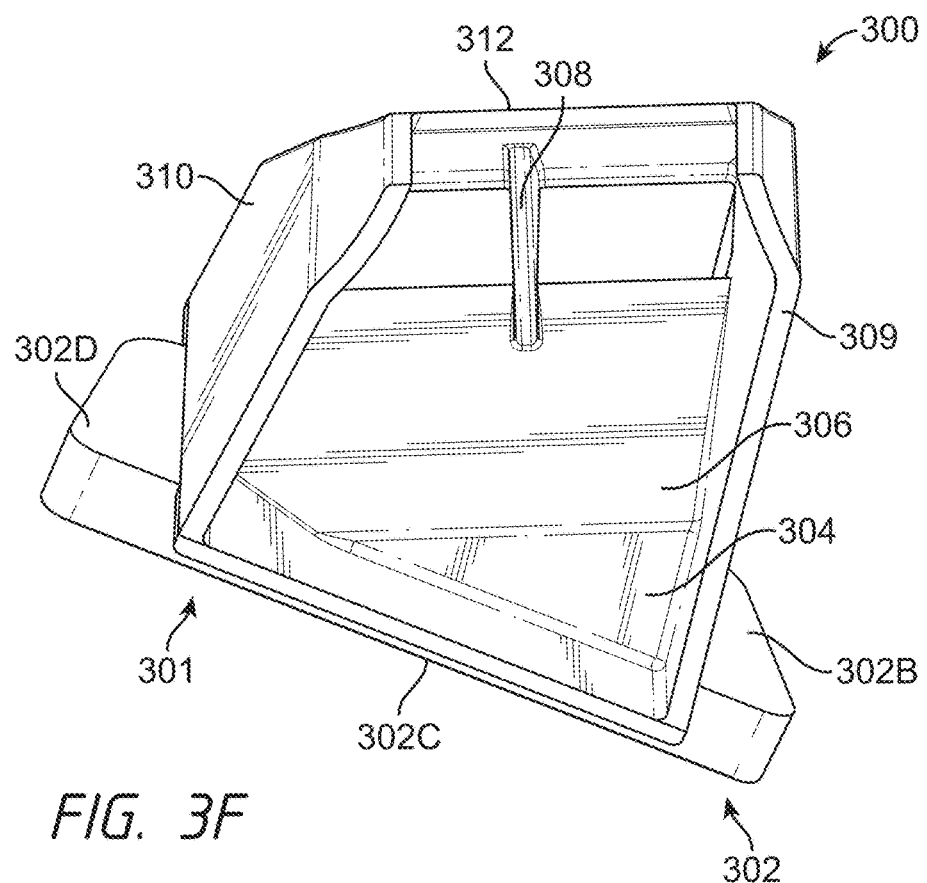
FIG. 3F shows a bottom-rear view of a model of the flow mixer of FIG. 3A.
Figure 3G:
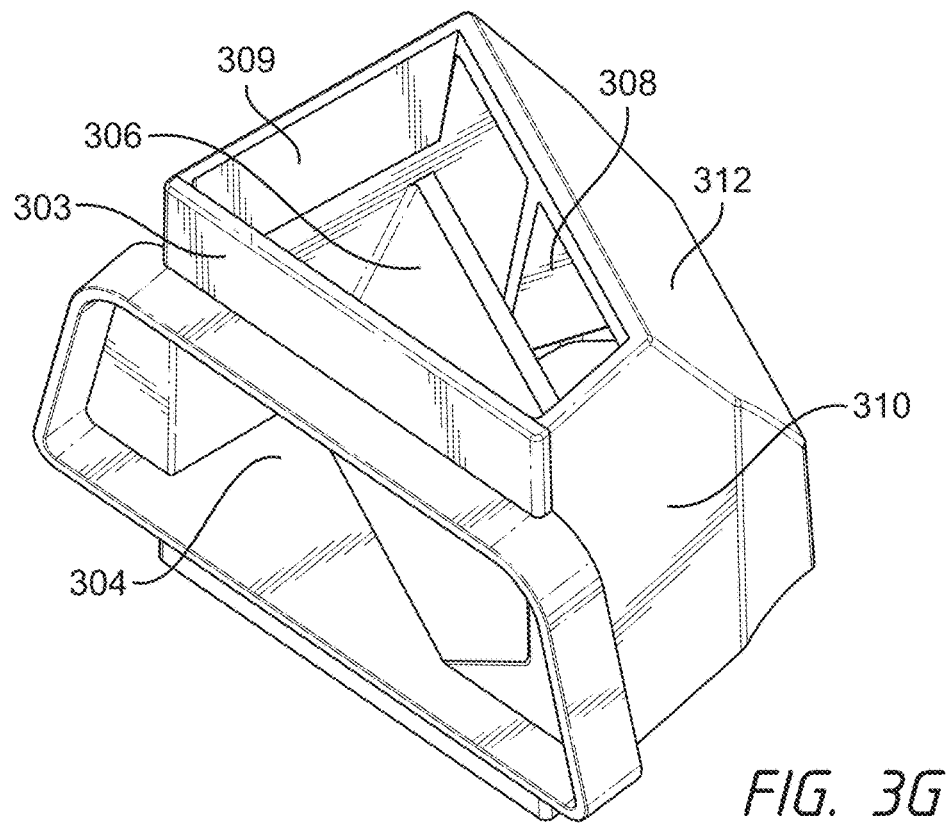
FIG. 3G shows a top-front view of the flow mixer of FIG. 3A.
Figure 3H:
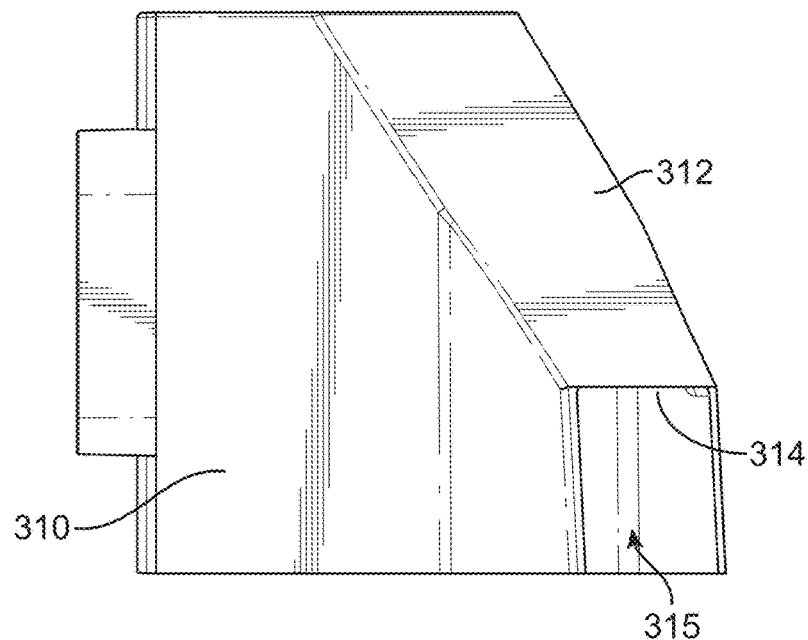
FIG. 3H shows a right side view of the flow mixer of FIG. 3A.
Figure 4:
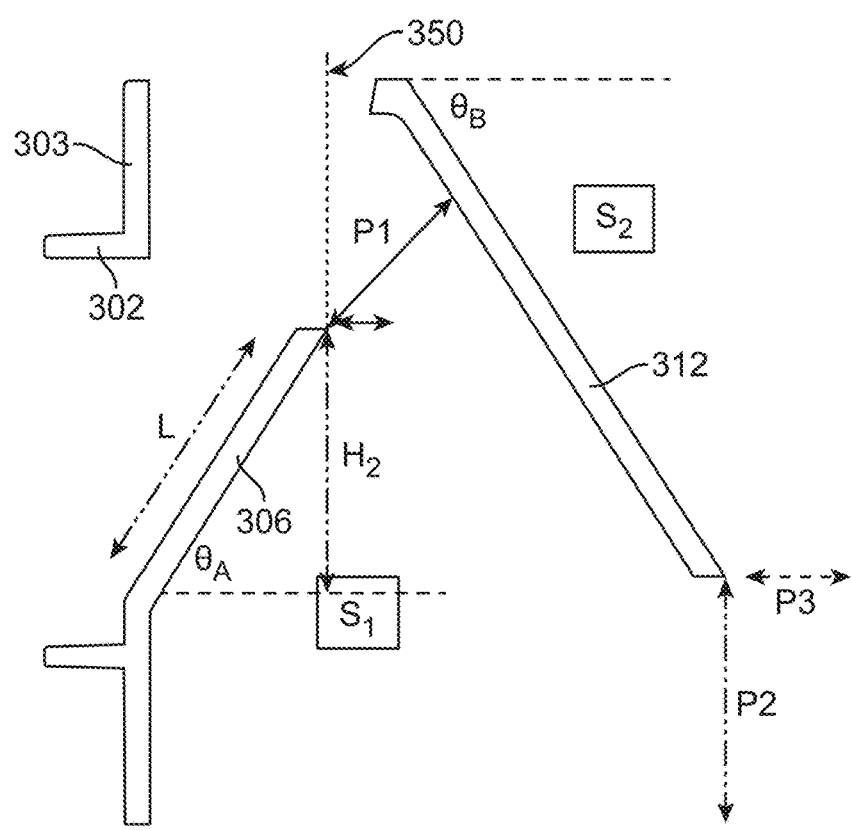
FIG. 4 shows a schematic of a cross-sectional view of a flow mixer.

FIG. 4 illustrates a schematic cross-sectional view similar to that of FIG. 3B. As shown, the first baffle 306 has a length L that is shorter than a length of the second baffle 312 such that the first baffle 306 does not entirely block the gases flow entering the flow mixer 300. As the horizontal distance between the first baffle 306 and second baffle 312 increases, the degree of mixing of gases decreases. Therefore, the horizontal distance between the first baffle 306 and the second baffle 312 should be reduced or minimized to promote greater mixing; however, the upstream edge of the second baffle 312 should be positioned beyond or downstream of line 350).

The pinch, indicated by P1 in FIG. 4, is the length of a line projected from the downstream edge of the first baffle 306 to an upstream face of the second baffle 312, where the line is perpendicular to the upstream face of the second baffle 312. The pinch causes the gases flow to speed up as the flow passes over the first baffle 306. Once the gases pass the first baffle 306 and pinch P1, the gases enter a larger space $S_1$ where the gases can expand and swirl. The size of the pinch P1 affects the mixing of gases. A smaller pinch P1 improves gas mixing, but increases the pressure drop within the system. A larger pinch P1 reduces the pressure drop, but may also reduce the effectiveness of gas mixing by the flow mixer 300. Therefore, the size of the pinch P1 can be selected based on considerations of the amount or degree of mixing desired or required and the pressure losses that can be tolerated within the system, as well as manufacturability. Some systems including a blower 106 having a motor are able to tolerate and compensate for some degree of pressure drop. Therefore, a smaller pinch P1 can be selected to increase mixing. However, if the pressure drop is too great, there is a risk of the motor overheating and/or wearing out more quickly due to having to work harder to compensate for the pressure drop and deliver gases to the patient at the appropriate pressure. Additionally, with relatively smaller patient interfaces, a greater pressure drop occurs across the interfaces, so the motor must operate and higher speeds to compensate for the pressure drop across the interface. In such a system, the motor may have more limited capacity to further compensate for a pressure drop across the flow mixer. A significant pressure drop may also be a concern where a large patient interface is used, as the system may not be able to reach the target flow rate.

In some embodiments, a height $H_2$ of the first baffle 306 is greater than half of the pinch P1. In some embodiments, the pinch P1 is less than the height $H_2$ of the first baffle 306, or the cross-sectional area of the pinch P1 is less than the surface area of the height $H_2$ of the first baffle 306, to increase the degree of mixing of the gases. In some embodiments, the pinch P1 is in the range of about ⅓ to ¼ of the height $H_2$ of the first baffle 306. In some embodiments, the pinch P1 is about a third of a total height of the flow mixer 300. The length L of the first baffle 306 affects the size of the pinch P1. For example, if the second baffle 312 remains constant, a greater length L of the first baffle 306 results in a smaller pinch P1.

An acute angle $\theta_A$ of the first baffle 306 relative to horizontal also contributes to mixing of the gases. The pinch P1 causes the gases to increase in speed as the gases pass through the pinch P1, and then the baffle angle $\theta_A$ allows the gases to expand and swirl in space $S_1$, which is partly created by the baffle angle $\theta_A$. In other words, the acute angle $\theta_A$ of the first baffle 306 creates a larger space $S_1$ and/or promotes greater swirling, and therefore more effective mixing, than a baffle angle of 90°. In some embodiments, the angle $\theta_A$ is in the range of about 30° to about 60°. In some embodiments, an angle $\theta_A$ of less than 30° may provide the gases with a relatively smooth flow path, which does not disturb the gas flow sufficiently for mixing to occur. The combined pinch P1 followed by swirl creates a desired mixing of the gases in the flow path. The swirl of the gases in space $S_1$ can be laminar rather than turbulent.

In some embodiments, the gas flow is laminar both upstream and downstream of the static mixer. The gas flow may also be substantially laminar within the static mixer, for example, at low flow rates, for example less than about 15 L min$^{-1}$. The static mixer 300 can substantially mix the gases without causing significant turbulence, e.g., at a low Reynolds number. For example, the static mixer 300 may operate at a Reynolds number less than 4000 such that the flow is non-turbulent. In some embodiments, the static mixer 300 operates at a Reynolds number between 35 and 2700, for example, between 70 and 1000. In some embodiments, the static mixer 300 operates at a Reynolds number between 70 and 2100 such that the flow is laminar. In some embodiments, the static mixer 300 operates at volumetric flow rates (standardized to 21.1° C./101325 Pa) of about 2 L min$^{-1}$ to 60 L min$^{-1}$.

A second pinch, indicated by P2, can be located following the second baffle 312. The second pinch P2 can be defined between the downstream edge of the second baffle 312 and a lower wall of the flow mixer 300 as shown in FIG. 4. Additionally or alternatively, a pinch P3 can be defined between the downstream edge of the second baffle 312 and an upstream edge of another component placed downstream in the flow path, for example, a diffuser such as a honeycomb as described in greater detail herein. After passing the second baffle 312 and second pinch P2, the gases can enter a larger space $S_2$ where the gases can expand and swirl. The second pinch P2 and the second baffle 312 can have relative dimensions and relationships to other features as those described herein with respect to pinch P1 and the first baffle 306. For example, a height of the second baffle 312 can be greater than half of the second pinch P2. In some embodiments, the second pinch P2 is less than the height of the second baffle 312, or the cross-sectional area of the second pinch P2 is less than the surface area of the height of the baffle, to increase the degree of mixing of the gases. In some embodiments, the second pinch P2 is in the range of about ⅓ to ¼ of the height of the second baffle 312. In some embodiments, the second pinch P2 is about a third of a total height of the flow mixer 300. The length of the second baffle 312 can affect the size of the second pinch P2. For example, a greater length of the second baffle 312 results in a smaller second pinch P2. An acute angle $\theta_B$ of the second baffle 312 relative to horizontal can also contribute to mixing of the gases. The second pinch P2 causes the gases to increase in speed as the gases pass through the second pinch P2, and then the baffle angle $\theta_B$ allows the gases to expand and swirl in space $S_2$, which is partly created by the baffle angle $\theta_B$. In other words, the acute angle $\theta_B$ of the second baffle 312 creates a larger space $S_2$ and/or promotes greater swirling, and therefore more effective mixing, than a baffle angle of 90°. In some embodiments, the angle $\theta_B$ is in the range of about 30° to about 60°. The baffle angles $\theta_A$ and $\theta_B$ of the first 306 and second 312 baffles, respectively, can be the same as or different from each other.

In embodiments in which the baffles 306, 312 are positioned at an angle relative to a plane perpendicular to the flow of gases entering the flow mixer 300, the baffles 306, 312 are preferably in the same plane such that the pinch P1 is symmetrical. In other words, when viewed from the top, for example as shown in FIG. 3A, the downstream edge of the first baffle 306 and upstream edge of the second baffle 312 are parallel to each other across their lengths such that the pinch P1 is uniform across the width of the flow mixer 300. If the downstream edge of the first baffle 306 and the upstream edge of the second baffle 312 are not parallel to each other, the gases may take the easiest path through the pinch P1 and will therefore not be as compressed, which reduces the degree of mixing.

Figure 5A:
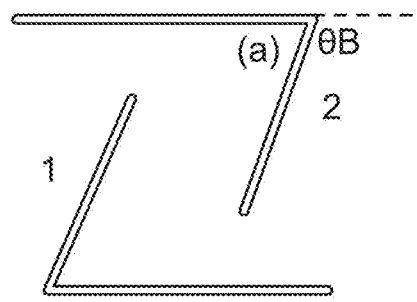
FIGS. 5A-5D show schematics of various baffle arrangements.
Figure 5B:
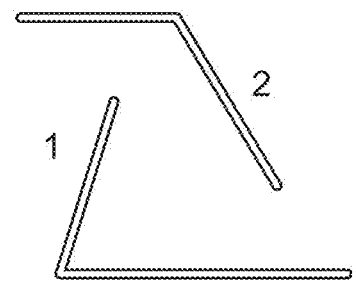
Figure 5C:
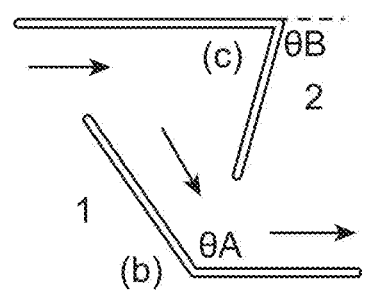
Figure 5D:
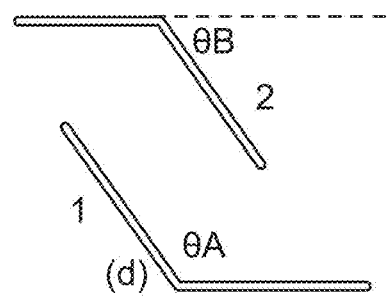

FIGS. 5A-5D illustrate various baffle configurations for flow mixers having a first baffle 1 and a second baffle 2. FIG. 5B illustrates the baffle arrangement illustrated in FIGS. 3A-4. FIG. 5A illustrates an embodiment in which the first baffle 1 is oriented similarly to the first baffle 306 of FIGS. 3A-4, and the second baffle 2 has an obtuse angle $\theta_B$. In some cases, the arrangement of FIG. 5B provides improved mixing compared to the arrangement of FIG. 5A, as in the arrangement of FIG. 5A, the obtuse angle $\theta_B$ may cause gases to become stagnant in area (a), which could cause a greater pressure drop in the system, and reduce the swirling downstream of the second baffle 2. FIG. 5C illustrates an embodiment in which the first baffle 1 has an obtuse angle $\theta_A$ and the second baffle 2 has an obtuse angle $\theta_B$. In some cases, the arrangements of FIGS. 5A and 5B may provide better mixing that the arrangement of FIG. 5C, as in the arrangement of FIG. 5C, the obtuse angles $\theta_A$ and $\theta_B$ may cause the gases to become stagnant in areas (b) and (c), which can result in less gases moving through the system and the gases following a more simple path (indicated by the arrows in FIG. 5C) and therefore being less likely to be sufficiently mixed. FIG. 5D illustrates an embodiment in which the first baffle 1 has an obtuse angle $\theta_A$ and the second baffle 2 has an obtuse angle $\theta_B$. In some cases, the arrangement of FIG. 5B may provide better mixing that the arrangement of FIG. 5D, as in the arrangement of FIG. 5D, the obtuse angle $\theta_A$ may cause gases to become stagnant in area (d).

Similar to the mixer 200 described in FIGS. 2A-2G, part or all of the flow mixer 300 may be integrally formed or moulded with a gas passageway of a respiratory therapy device (or accessory or peripheral thereof) or may be in a form of a separate piece that may be inserted into a gas passageway of a respiratory therapy device (or accessory or peripheral thereof). Additionally, some or all of the internal surfaces of either the mixer 200 or the flow mixer 300 may be rough, or the mixer 200 or flow mixer 300 may otherwise have a patterned or random variation of thickness along the gas contact surfaces of the mixers 200, 300, including along the baffles 208, 212, 306, 312. The average magnitude of the roughness may be, for example, from about 0% to about 20%, or from about 4% to about 16%, or from about 8% to about 12%, or about 10%. Rough internal surfaces can help to increase the vorticity of flow passing through the mixers 200, 300 which can improve gas mixing.

As implied above and elsewhere in this disclosure, the flow mixer 300 as shown in FIGS. 3A-3F may be used as follows. Gases passing through the flow mixer 300 may enter the flow mixer 300 via the gases entry region 301 externally bounded by the flange 302 and upwardly (and in some configurations at a horizontal offset) along the first baffle 306. The gas flow may then be bisected or otherwise cut by the bridge 308 and move downwardly (and in some configurations again at another horizontal offset) along the second baffle 308, which may also force the gas flow inwardly. Gases may then pass off the edge region 314 and out the gases exit region 315. The gas flow passing out the gases exit region 315 of the flow mixer 300 may be better mixed at least in a vertical direction along a given cross-section of a gas passageway than gases entering the flow mixer 300 through the gases entry region 301.

Figure 6:
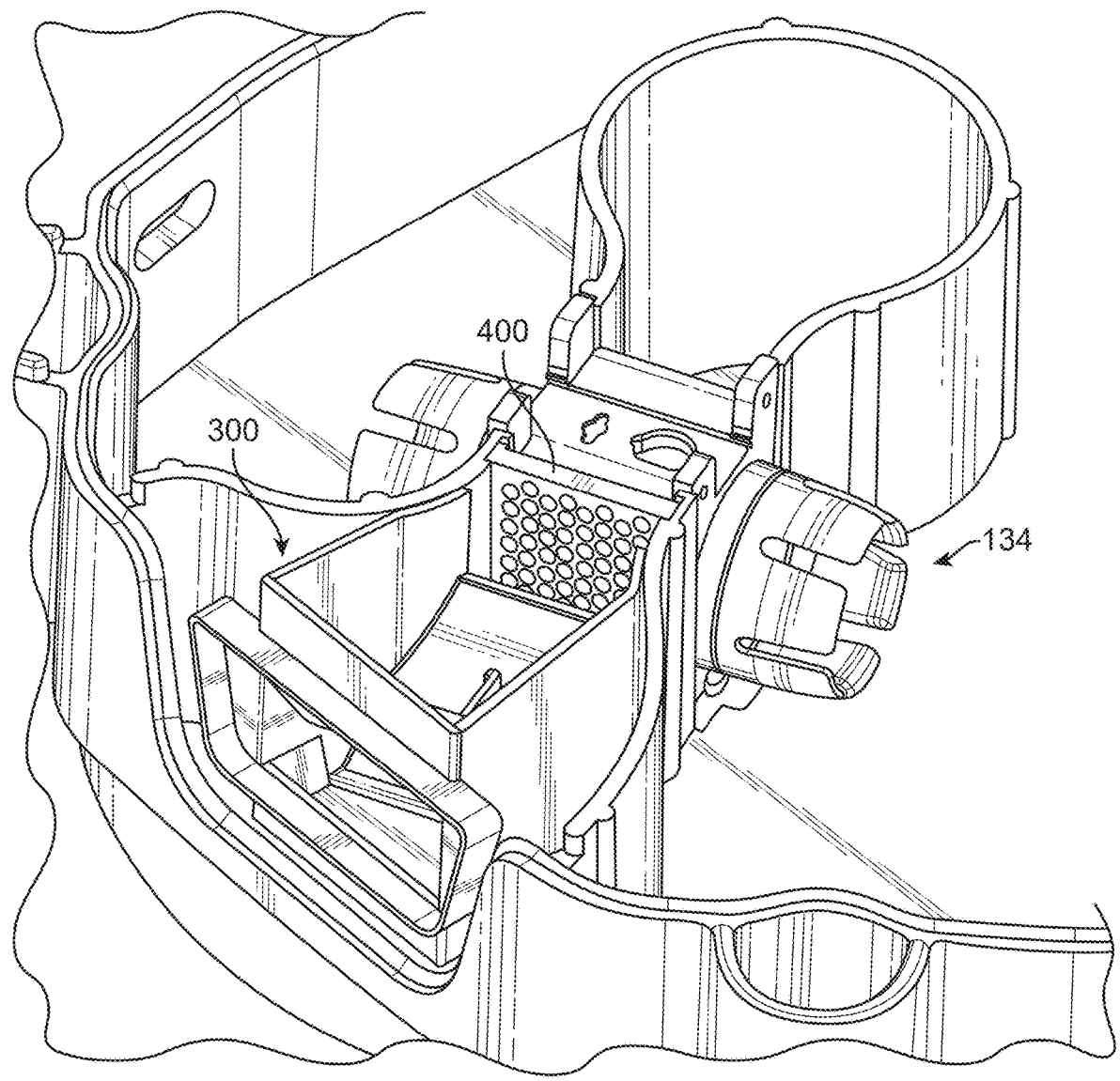
FIG. 6 shows a bottom perspective view of the flow mixer of FIGS. 3A-3H, a honeycomb, and a sensor disposed within a gases source.
Figure 7:
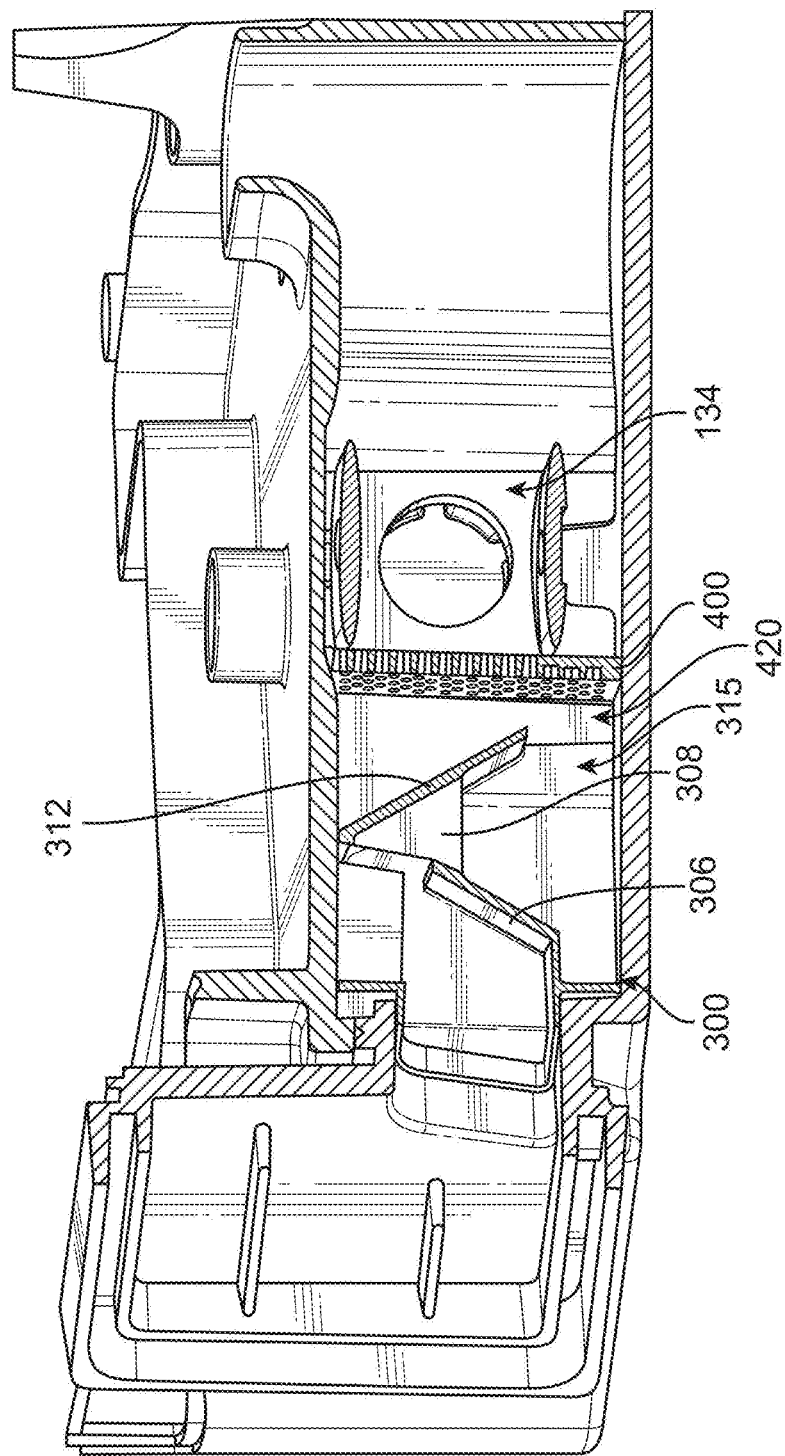
FIG. 7 shows a cross-sectional view of FIG. 6.

FIGS. 6 and 7 show the flow mixer 300 disposed within a flow generator or gases source. FIG. 6 illustrates a bottom perspective view and FIG. 7 illustrates a cross-sectional view. A diffuser can be disposed downstream of the flow mixer 300 between the flow mixer 300 and the gas composition sensor 134, which may be an ultrasonic transducer. In the illustrated embodiment, the diffuser is a honeycomb 400. In use, gases flow through the static mixer 300, through the honeycomb 400, and past the sensor 134. In the illustrated embodiment, the honeycomb 400 is positioned adjacent the sensor 134 and there is a gap 420 between the outlet 315 of the flow mixer 300 and the honeycomb 400. As described in greater detail herein, a pinch P3 can be the length of a line extending from the downstream edge of the second baffle 312 to the upstream side of the honeycomb 400, where the line extends perpendicularly to the honeycomb 400. The honeycomb 400 can advantageously act as an additional baffle to further encourage swirl of the gases and can help distribute the gases. There is a pressure drop across the honeycomb 400, which can allow the upstream gases to equilibrate and provide a more even flow.

Figure 8A:
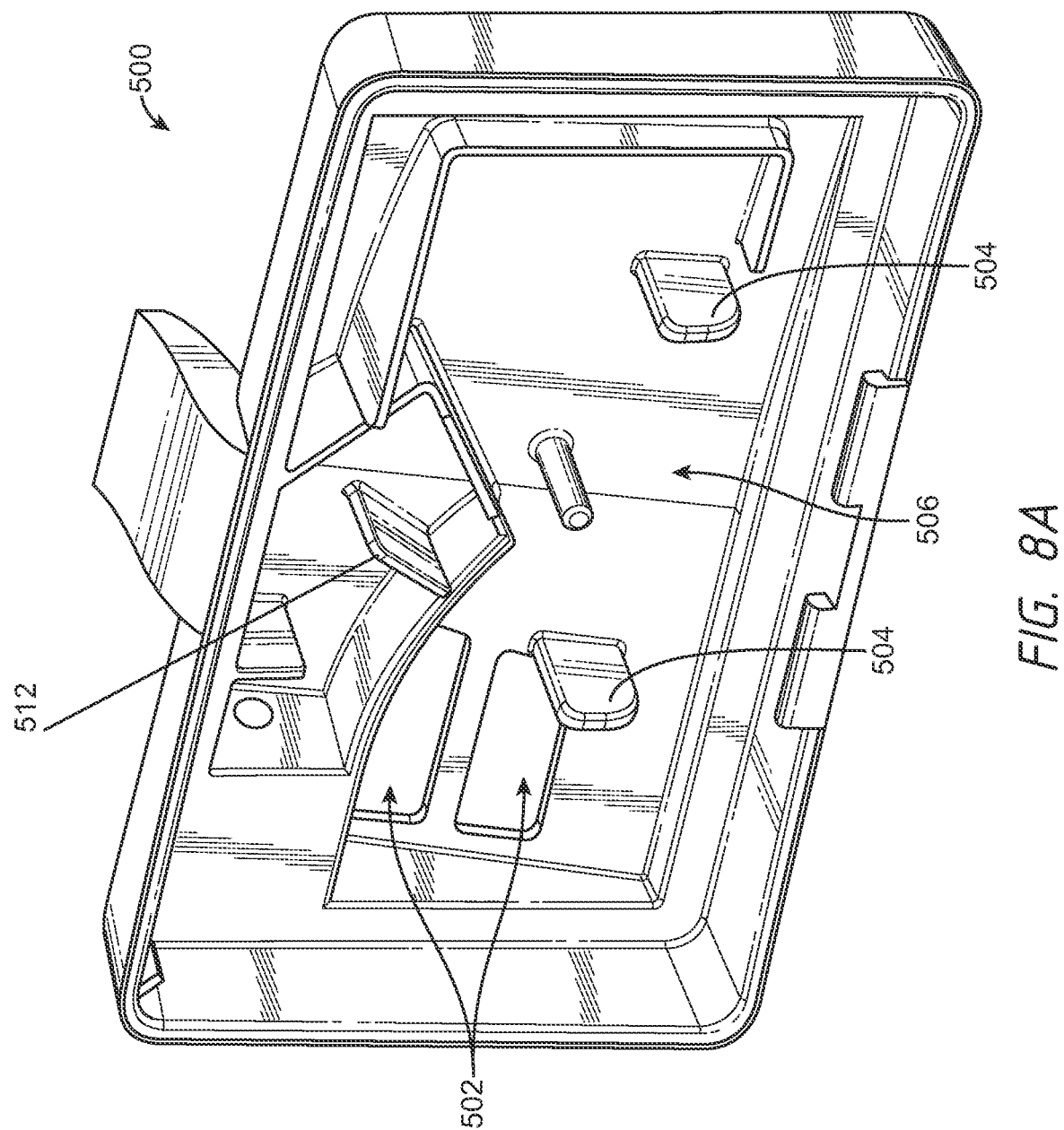
FIG. 8A shows a rear perspective view of an example embodiment of a filter cover.
Figure 8B:
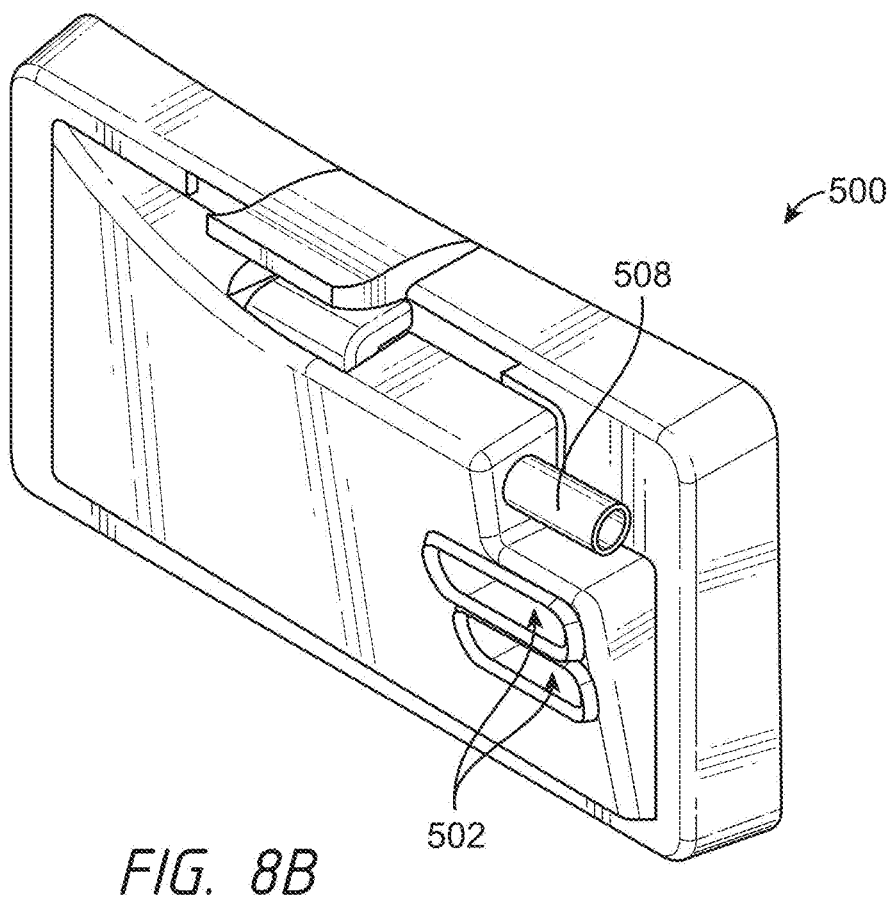
FIG. 8B shows a front perspective view of the filter cover of FIG. 8A.

In some embodiments, a flow generator or gases source can include a filter media and a filter cover upstream of the static mixer, for example, at or near the first gas inlet 102. FIGS. 8A and 8B illustrate an example embodiment of a filter cover 500. Gases can be drawn into the filter cover 500 and the gases source through apertures 502. The filter cover 500 includes an inlet pipe 508 that receives gases from the second gas source 128, e.g., via a conduit or tubing extending between and connected to the second gas source 128 and the inlet pipe 508. The filter cover comprises a passageway extending from the inlet pipe to the cavity. The passageway comprises at least one baffle 512. The filter cover 500 can include prongs 504 extending rearwardly from a front surface of the filter cover 500 to help push the filter media in fully and inhibit the filter media from sagging. In the illustrated embodiment, the filter cover 500 includes two prongs 504. The prongs 504 can also create or define a cavity 506 in the filter cover 500 between the filter cover 500 and the filter media. The incoming gases can swirl within the cavity 506, which can help promote mixing of gases drawn in through apertures 502 and gases received from the second gas source 128 through the inlet pipe 508. The gases can then pass through the static mixer, which can cause further mixing of the gases.

Figure 9:
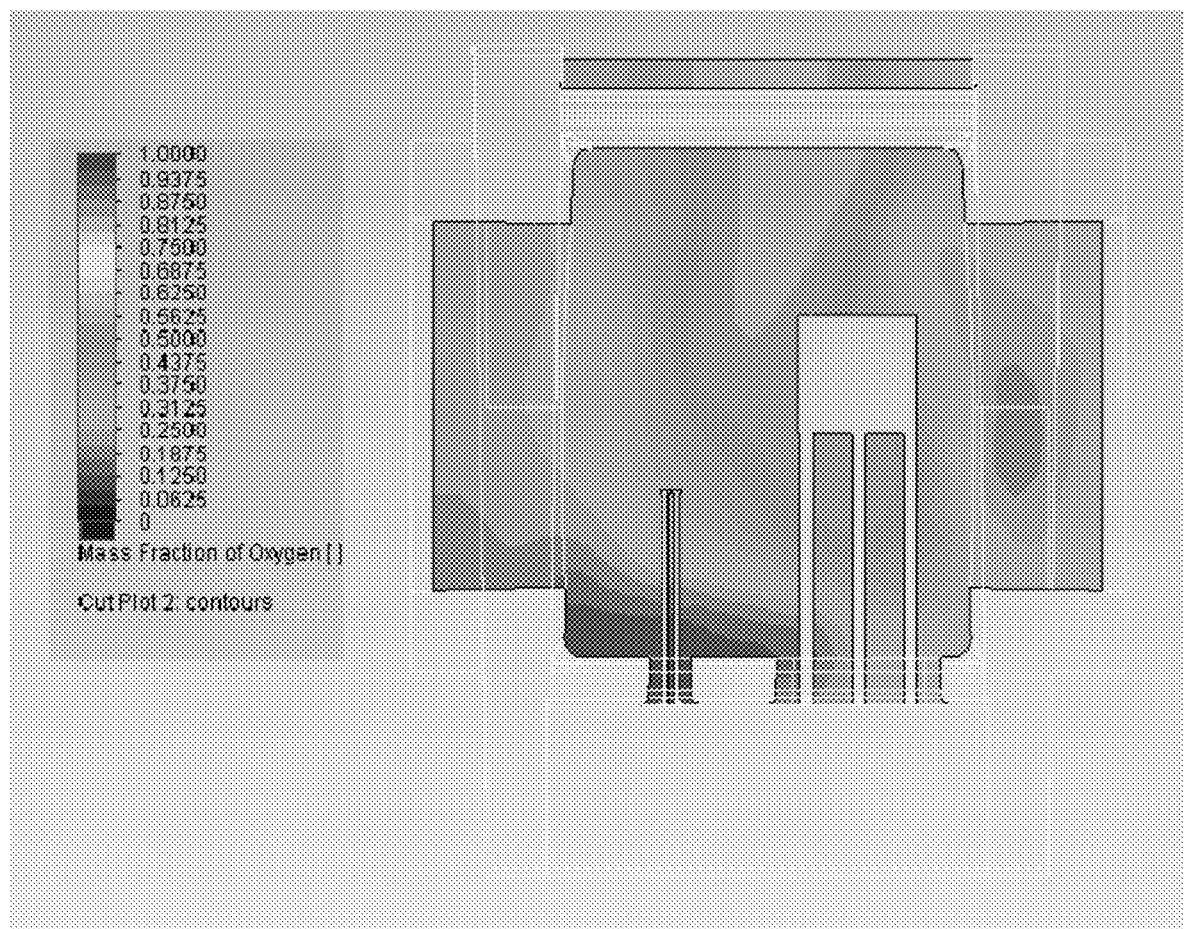
FIG. 9 shows results of computational fluid dynamics showing gas mixing in a section of a flow path through an ultrasonic transducer.

In various embodiments, the static mixers according to the present disclosure cause sufficient gas mixing for the sensor 134, such as ultrasonic transducer 220, to provide more accurate readings. In some embodiments, the static mixers cause sufficient gas mixing such that the local oxygen fraction in any portion of the gas flow being sampled by the sensor is believed to be within ±30% $O_2$, ±20% $O_2$, or ±10% $O_2$ of the bulk oxygen fraction of the gas (e.g., based on computational fluid dynamics and/or experimental results). In other words, the oxygen fraction in the region where sensor readings are taken does not vary by more than ±30%, ±20%, or ±10% from the actual average fraction of oxygen. In some embodiments, the static mixers cause sufficient gas mixing such that the mean oxygen fraction measured across a predetermined path is within ±6% $O_2$ of the bulk oxygen fraction of the gas, ±5% $O_2$ of the bulk oxygen fraction of the gas, ±4% $O_2$ of the bulk oxygen fraction of the gas, ±3% $O_2$ of the bulk oxygen fraction of the gas, ±2% $O_2$ of the bulk oxygen fraction of the gas, ±1% $O_2$ of the bulk oxygen fraction of the gas, ±0.9% $O_2$ of the bulk oxygen fraction of the gas, or ±0.86% $O_2$ of the bulk oxygen fraction of the gas. In some embodiments, the predetermined path is the acoustic path of the ultrasonic transducer 220. In other words, the net error introduced to the sensor oxygen measurement due to poor mixing may be less than ±6%, ±5%, ±4%, ±3%, ±2%, ±1%, ±0.9%, or ±0.86%. FIG. 9 illustrates results of computational fluid dynamics showing the fraction of $O_2$ (representing the mixing of the gases) across a cross section of the flow path through the ultrasonic transducer 220. As used herein, "substantially uniformly mixed" means that gases are sufficiently mixed to allow for more accurate sensor readings, which can mean the mean oxygen fraction measured across a predetermined path is within ±6%, 5%, 4%, 3%, 2%, 1%, 0.9%, or 0.86% $O_2$ of the bulk oxygen fraction of the gas. In an embodiment, the predetermined path may be the acoustic path of an ultrasonic transducer.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Recitation of ranges herein is merely intended to serve as a shorthand method of referring individually to each separate sub-range or value falling within the range, unless otherwise indicated herein, and each separate sub-range or value is incorporated into the specification as if it were individually recited herein.

As used herein, directional terms, such as "horizontal," "vertical," "upwards," and "downwards," "right," "left," and the like, are relative terms and are provided simply for ease of references. Unless otherwise apparent from the particular usage, such terms should not be strictly construed. For example, if the static mixer 200 is rotated 90° clockwise in use, for example, to better fit the system in which it is used, the first sloping section 208 might extend at an angle left and forward and the second sloping section 212 might extend at an angle right and forward. Thus, while certain features, aspects and advantages of the present invention may be described with reference to certain directional and angular relationship, others are possible and are explicitly contemplated to be within the scope of the present disclosure.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory therapy system comprising:
 a flow generator within a housing;
 a flow mixer configured to mix a first gas comprising ambient air and a second gas comprising a therapeutic gas by inducing swirling flow regions;
 an ultrasonic sensor positioned in a gas passageway downstream of the flow mixer, wherein the flow mixer is configured to mix the first gas and the second gas to enable the ultrasonic sensor to provide more reliable readings, wherein the ultrasonic sensor comprises an ultrasonic transducer configured to emit and/or receive waves in a direction substantially perpendicular to a direction of gas mixing by the flow mixer;
 a humidifier downstream of the flow generator;
 a filter cover positioned upstream of the flow mixer and containing a filter media, wherein the filter cover comprises one or more apertures and a filter inlet pipe, wherein the first gas is configured to pass through the one or more apertures of the filter cover, and wherein the second gas is configured to pass through the filter inlet pipe; and a cavity between the filter cover and the filter media for mixing the first gas and the second gas;

wherein the filter cover comprises a passageway extending from the filter inlet pipe to the cavity, the passageway comprising at least one baffle.

2. The respiratory therapy system of claim 1, wherein the ultrasonic sensor is configured to measure a concentration of at least one gas flowing in the gas passageway downstream of the flow mixer.

3. The respiratory therapy system of claim 1, wherein the flow mixer is configured to substantially uniformly mix the first gas and the second gas in a vertical direction and/or a horizontal direction.

4. The respiratory therapy system of claim 1, wherein a local oxygen fraction in a gas flow formed by mixing of the first gas and the second gas in a region of the ultrasonic sensor is within ±10% $O_2$ of a bulk oxygen fraction of the gas flow.

5. The respiratory therapy system of claim 1, further comprising a diffuser positioned between the flow mixer and the ultrasonic sensor.

6. The respiratory therapy system of claim 1, wherein the filter cover comprises prongs extending rearwardly from a front wall of the filter cover, wherein the prongs are configured to hold filter media in place and create the cavity between the filter cover and the filter media.

7. The respiratory therapy system of claim 6, wherein the prongs are configured to push the filter media in fully.

8. The respiratory therapy system of claim 6, wherein the prongs are configured to prevent the filter media from sagging.

9. The respiratory therapy system of claim 6, wherein the cavity between the filter cover and the filter media is defined by the rearwardly extending prongs of the filter cover.

10. The respiratory therapy system of claim 1, wherein the flow mixer comprises at least one baffle configured to induce the swirling flow regions.

11. The respiratory therapy system of claim 1, wherein the flow mixer comprises a first baffle and a second baffle, wherein the first baffle is spaced apart from the second baffle.

12. The respiratory therapy system of claim 11, wherein the first baffle extends in a downstream direction at a first angle offset from a horizontal plane and the second baffle extends in the downstream direction at a second angle offset from the horizontal plane.

13. The respiratory therapy system of claim 12, wherein the first angle and the second angle are offset on opposing sides of the horizontal plane.

14. The respiratory therapy system of claim 11, wherein the first baffle causes a gas flow through the flow mixer to move upwards and then sharply turn at a downstream edge of the first baffle.

15. The respiratory therapy system of claim 14, wherein the second baffle causes the gas flow through the flow mixer to move downwards and then sharply turn at a downstream edge of the second baffle.

16. The respiratory therapy system of claim 11, wherein the flow mixer comprises a pinch defined between a downstream edge of the first baffle and an upstream face of the second baffle.

17. The respiratory therapy system of claim 16, wherein a length of the pinch is less than a height of the first baffle.

18. The respiratory therapy system of claim 16, wherein the flow mixer comprises a second pinch defined between a downstream edge of the second baffle and a bottom wall of the flow mixer.

19. The respiratory therapy system of claim 11, wherein the first baffle extends in a downstream direction at a first angle offset from a first vertical plane and the second baffle extends in the downstream direction at a second angle offset from a second vertical plane.

20. The respiratory therapy system of claim 19, wherein the first angle and the second angle are the same.

21. The respiratory therapy system of claim 19, wherein the first angle and the second angle are different.

22. The respiratory therapy system of claim 1, wherein the passageway is a curved passageway.

23. The respiratory therapy system of claim 1, wherein the at least one baffle is a pair of baffles.

* * * * *